(12) United States Patent
Franklin et al.

(10) Patent No.: US 12,011,172 B2
(45) Date of Patent: Jun. 18, 2024

(54) OCCLUSION CATHETER SYSTEM FOR FULL OR PARTIAL OCCLUSION

(71) Applicant: Prytime Medical Devices, Inc., Boerne, TX (US)

(72) Inventors: Curtis J. Franklin, Lakewood, CO (US); Jeremy Reynolds, Lakewood, CO (US); Eric Pointer, Lakewood, CO (US); Matthew Garland, Lakewood, CO (US); Todd J. Krummenacher, Lakewood, CO (US)

(73) Assignee: PRYTIME MEDICAL DEVICES, INC., Boerne, TX (US)

( * ) Notice: Subject to any disclaimer, the term of this patent is extended or adjusted under 35 U.S.C. 154(b) by 498 days.

(21) Appl. No.: 17/265,352

(22) PCT Filed: Aug. 6, 2019

(86) PCT No.: PCT/US2019/045252
§ 371 (c)(1),
(2) Date: Feb. 2, 2021

(87) PCT Pub. No.: WO2020/033372
PCT Pub. Date: Feb. 13, 2020

(65) Prior Publication Data
US 2021/0290243 A1 Sep. 23, 2021

Related U.S. Application Data

(60) Provisional application No. 62/714,863, filed on Aug. 6, 2018.

(51) Int. Cl.
*A61B 17/12* (2006.01)
*A61M 25/00* (2006.01)
*A61M 25/10* (2013.01)

(52) U.S. Cl.
CPC .. *A61B 17/12036* (2013.01); *A61B 17/12031* (2013.01); *A61B 17/12136* (2013.01);
(Continued)

(58) Field of Classification Search
CPC ........ A61B 17/12036; A61B 17/12031; A61B 17/12136; A61B 2562/0247;
(Continued)

(56) References Cited

U.S. PATENT DOCUMENTS 2,156,289 A 5/1939 Hoy
4,464,172 A 8/1984 Lichtenstein
(Continued)

FOREIGN PATENT DOCUMENTS

EP 1094861 B1 4/2005
EP 1658808 A1 5/2006
(Continued)

OTHER PUBLICATIONS

Int'l Search Report and Written Opinion issued Jun. 8, 2022 in Int'l Application No. PCT/US2022/020704.
(Continued)

*Primary Examiner* — Lauren P Farrar
(74) *Attorney, Agent, or Firm* — Panitch Schwarze Belisario & Nadel LLP

(57) ABSTRACT

An occlusion catheter system for full or partial occlusion of a vessel includes an occlusion balloon. The balloon is positioned in a folded, uninflated configuration around a central shaft, a proximal shaft, and a distal shaft of the occlusion catheter system, having an outer diameter less than seven French. The balloon is constructed of a semi-compliant or non-compliant material and is sized to have a blown diameter between approximately ten percent to sixty percent greater than the inner diameter of the vessel, whereby an outer surface of the balloon comes into full (Continued)

diametric contact with an inner surface of the vessel upon partial inflation of the balloon and folds are formed in the outer surface of the balloon. The folds define flow channels with inner surfaces of the vessel or with portions of the outer surface of the balloon that allow partial blood flow past the balloon.

15 Claims, 16 Drawing Sheets

(52) U.S. Cl.
CPC ............... *A61M 25/10185* (2013.11); *A61B 2562/0247* (2013.01); *A61M 2025/0008* (2013.01); *A61M 2025/1004* (2013.01)

(58) Field of Classification Search
CPC ... A61B 2017/00022; A61B 2017/00115; A61B 2017/00199; A61B 2090/064; A61B 17/12109; A61M 25/10185; A61M 2025/0008; A61M 2025/1004; A61M 25/1002; A61M 25/10186; A61M 2025/1052; A61M 2025/1079
See application file for complete search history.

(56) References Cited

U.S. PATENT DOCUMENTS

| | | |
|---|---|---|
| 4,713,888 A | 12/1987 | Broselow |
| 4,777,951 A | 10/1988 | Cribier et al. |
| 4,823,469 A | 4/1989 | Broselow |
| 4,865,549 A | 9/1989 | Sonsteby |
| 4,926,885 A | 5/1990 | Hinkle |
| 4,983,166 A | 1/1991 | Yamawaki |
| 5,047,045 A | 9/1991 | Arney et al. |
| 5,087,246 A | 2/1992 | Smith |
| 5,135,494 A | 8/1992 | Engelson et al. |
| 5,158,529 A | 10/1992 | Kanai |
| 5,169,386 A | 12/1992 | Becker et al. |
| 5,250,070 A | 10/1993 | Parodi |
| 5,282,479 A | 2/1994 | Havran |
| 5,295,995 A | 3/1994 | Kleiman |
| 5,320,605 A | 6/1994 | Sahota |
| 5,383,856 A | 1/1995 | Bersin |
| 5,425,711 A | 6/1995 | Ressemann |
| 5,447,503 A | 9/1995 | Miller |
| 5,505,702 A | 4/1996 | Arney |
| 5,522,400 A | 6/1996 | Williams |
| 5,554,121 A | 9/1996 | Ainsworth |
| 5,558,644 A | 9/1996 | Boyd et al. |
| 5,571,093 A | 11/1996 | Cruz et al. |
| 5,609,606 A | 3/1997 | O'Boyle |
| 5,718,678 A | 2/1998 | Fleming, III |
| 5,738,652 A | 4/1998 | Boyd et al. |
| 5,911,702 A | 6/1999 | Romley et al. |
| 6,007,517 A | 12/1999 | Anderson |
| 6,011,988 A | 1/2000 | Lynch et al. |
| 6,013,019 A | 1/2000 | Fischell et al. |
| 6,013,055 A | 1/2000 | Bampos et al. |
| 6,102,930 A | 8/2000 | Simmons, Jr. |
| 6,113,579 A | 9/2000 | Eidenschink et al. |
| 6,129,737 A | 10/2000 | Hamilton et al. |
| 6,146,370 A | 11/2000 | Barbut |
| 6,161,547 A | 12/2000 | Barbut |
| 6,165,199 A | 12/2000 | Barbut |
| 6,190,356 B1 | 2/2001 | Bersin |
| 6,231,572 B1 | 5/2001 | Hart et al. |
| 6,248,121 B1 | 6/2001 | Nobles |
| 6,280,434 B1 | 8/2001 | Kinoshita et al. |
| 6,423,031 B1 | 7/2002 | Donlon |
| 6,453,572 B2 | 9/2002 | Cross et al. |
| 6,575,932 B1 | 6/2003 | O'Brien et al. |
| 6,579,221 B1 | 6/2003 | Peterson |
| 6,602,270 B2 | 8/2003 | Leschinsky et al. |
| 6,656,153 B1 | 12/2003 | Sakai et al. |
| 6,666,814 B2 | 12/2003 | Downey et al. |
| 6,669,679 B1 | 12/2003 | Savage et al. |
| 6,679,860 B2 | 1/2004 | Stiger |
| 6,695,811 B2 | 2/2004 | Samson et al. |
| 6,719,270 B2 | 4/2004 | Ozawa |
| 6,719,720 B1 | 4/2004 | Voelker et al. |
| 6,733,513 B2 | 5/2004 | Boyle et al. |
| 6,735,532 B2 | 5/2004 | Freed et al. |
| 6,736,790 B2 | 5/2004 | Barbut et al. |
| 6,746,462 B1 | 6/2004 | Selmon et al. |
| 6,796,959 B2 | 9/2004 | Davis et al. |
| 6,936,056 B2 | 8/2005 | Nash et al. |
| 6,979,318 B1 | 12/2005 | McDonald et al. |
| 7,341,571 B1 | 3/2008 | Harris et al. |
| 7,434,326 B2 | 10/2008 | Gifford |
| 7,503,904 B2 | 3/2009 | Choi |
| 7,503,909 B2 | 3/2009 | Kusu et al. |
| 7,763,043 B2 | 7/2010 | Goodin et al. |
| 7,892,469 B2 | 2/2011 | Lim et al. |
| 7,909,810 B2 | 3/2011 | Noone |
| 7,951,186 B2 | 5/2011 | Eidenschink et al. |
| 7,951,819 B2 | 5/2011 | Niculescu-Duvaz et al. |
| 7,959,644 B2 | 6/2011 | Shriver |
| 8,021,330 B2 | 9/2011 | McAndrew |
| 8,088,103 B2 | 1/2012 | Teeslink et al. |
| 8,162,879 B2 | 4/2012 | Hattangadi et al. |
| 8,241,241 B2 | 8/2012 | Evans et al. |
| 8,262,611 B2 | 9/2012 | Teeslink et al. |
| 8,419,648 B2 | 4/2013 | Corl et al. |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,655,798 B2 | 2/2014 | Humphrey et al. |
| 8,672,868 B2 | 3/2014 | Simons |
| 8,747,358 B2 | 6/2014 | Trombley, III et al. |
| 8,814,900 B2 | 8/2014 | Fleming, III |
| 8,900,214 B2 | 12/2014 | Nance et al. |
| 8,948,848 B2 | 2/2015 | Merhi |
| 8,951,565 B2 | 2/2015 | McCarthy |
| 9,131,874 B2 | 9/2015 | Eliason et al. |
| 9,211,396 B2 | 12/2015 | Aboytes |
| D748,257 S | 1/2016 | Franklin |
| 9,414,843 B2 | 8/2016 | Pavcnik et al. |
| 9,474,882 B2 | 10/2016 | Franklin |
| 9,687,333 B2 | 6/2017 | Angel et al. |
| 10,368,872 B2 | 8/2019 | Franklin et al. |
| 2001/0038807 A1* | 11/2001 | Barbut ............... A61M 1/3613 422/44 |
| 2002/0007146 A1 | 1/2002 | Omaleki et al. |
| 2002/0062119 A1 | 5/2002 | Zadno-Azizi |
| 2002/0081406 A1 | 6/2002 | Wang et al. |
| 2002/0193735 A1 | 12/2002 | Stiger |
| 2003/0032974 A1 | 2/2003 | Leschinsky et al. |
| 2003/0083579 A1 | 5/2003 | Aita et al. |
| 2003/0167038 A1 | 9/2003 | Yozu et al. |
| 2004/0039332 A1 | 2/2004 | Kantor |
| 2004/0073162 A1 | 4/2004 | Bleam et al. |
| 2004/0082935 A1 | 4/2004 | Lee et al. |
| 2004/0254528 A1 | 12/2004 | Adams et al. |
| 2005/0059931 A1 | 3/2005 | Garrison et al. |
| 2005/0148812 A1 | 7/2005 | Nigroni et al. |
| 2005/0261725 A1 | 11/2005 | Crawford et al. |
| 2007/0043307 A1 | 2/2007 | Raulerson et al. |
| 2007/0043409 A1 | 2/2007 | Brian et al. |
| 2007/0129466 A1 | 6/2007 | Kagawa et al. |
| 2007/0135830 A1 | 6/2007 | Schaeffer |
| 2007/0219466 A1 | 9/2007 | Tremulis et al. |
| 2007/0219488 A1 | 9/2007 | Francescatti |
| 2008/0027356 A1 | 1/2008 | Chen et al. |
| 2008/0082046 A1 | 4/2008 | Kato et al. |
| 2008/0082119 A1 | 4/2008 | Vitullo |
| 2008/0097300 A1 | 4/2008 | Eskaros et al. |
| 2008/0200839 A1 | 8/2008 | Bunch et al. |
| 2008/0243067 A1 | 10/2008 | Rottenberg et al. |
| 2008/0243221 A1 | 10/2008 | Arcand |
| 2008/0262477 A1 | 10/2008 | Djaladat |
| 2008/0287786 A1 | 11/2008 | Lentz |
| 2009/0018500 A1 | 1/2009 | Carter et al. |

(56) References Cited

U.S. PATENT DOCUMENTS

| | | |
|---|---|---|
| 2009/0026595 A1 | 1/2009 | Kadoi |
| 2009/0062666 A1 | 3/2009 | Roteliuk |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0113939 A1 | 5/2010 | Mashimo et al. |
| 2010/0204712 A1 | 8/2010 | Mallaby |
| 2010/0234915 A1 | 9/2010 | Herlich et al. |
| 2010/0241008 A1 | 9/2010 | Belleville et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2011/0144742 A1 | 6/2011 | Madrid et al. |
| 2011/0172696 A1 | 7/2011 | Jeffrey et al. |
| 2011/0196412 A1 | 8/2011 | Levit et al. |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0209176 A1 | 8/2012 | Anderson |
| 2012/0215166 A1 | 8/2012 | Barki |
| 2012/0271231 A1 | 10/2012 | Agrawal |
| 2012/0302994 A1 | 11/2012 | Wilson et al. |
| 2013/0102926 A1 | 4/2013 | Eliason et al. |
| 2013/0102929 A1 | 4/2013 | Haight et al. |
| 2013/0172786 A1 | 7/2013 | Olson et al. |
| 2013/0190619 A1 | 7/2013 | Nudel |
| 2013/0281869 A1 | 10/2013 | Barbut et al. |
| 2013/0289607 A1 | 10/2013 | Pedersen et al. |
| 2013/0338637 A1 | 12/2013 | Fischer, Jr. et al. |
| 2014/0221898 A1 | 8/2014 | Kurrus et al. |
| 2014/0243873 A1* | 8/2014 | Franklin .......... A61B 17/12136 606/194 |
| 2014/0249504 A1 | 9/2014 | Franklin et al. |
| 2014/0316012 A1 | 10/2014 | Freyman et al. |
| 2014/0364835 A1 | 12/2014 | Allen et al. |
| 2014/0378869 A1 | 12/2014 | Sela et al. |
| 2015/0012031 A1 | 1/2015 | Rago et al. |
| 2015/0039012 A1 | 2/2015 | Solar et al. |
| 2015/0272732 A1 | 10/2015 | Tilson et al. |
| 2015/0367098 A1 | 12/2015 | Aggerholm et al. |
| 2016/0000446 A1 | 1/2016 | Eliason et al. |
| 2016/0051386 A1 | 2/2016 | Haarmann-Thiemann |
| 2016/0375230 A1 | 12/2016 | Lee et al. |
| 2019/0076152 A1 | 3/2019 | Franklin et al. |
| 2019/0366046 A1 | 12/2019 | Klocke et al. |
| 2020/0022587 A1 | 1/2020 | Glover et al. |
| 2021/0138187 A1 | 5/2021 | Tilson et al. |
| 2021/0290243 A1 | 9/2021 | Franklin et al. |

FOREIGN PATENT DOCUMENTS

| | | |
|---|---|---|
| EP | 1911484 A2 | 4/2008 |
| EP | 2389974 A1 | 11/2011 |
| EP | 2716323 A1 | 4/2014 |
| EP | 2837402 A2 | 2/2015 |
| GB | 2297259 A | 7/1996 |
| JP | H 03198868 A | 8/1991 |
| JP | H03280962 A | 12/1991 |
| JP | H 09-164208 A | 6/1997 |
| JP | H1080497 A | 3/1998 |
| JP | 2000217922 A | 8/2000 |
| JP | 2002505165 A | 2/2002 |
| JP | 2003535652 A | 12/2003 |
| JP | 200714820 A | 1/2007 |
| JP | 2008546471 A | 12/2008 |
| JP | 2011245300 A | 12/2011 |
| WO | 9220398 A1 | 11/1992 |
| WO | 9713542 A1 | 4/1997 |
| WO | 9725093 A1 | 7/1997 |
| WO | 9834670 A2 | 8/1998 |
| WO | 1999/24105 A2 | 5/1999 |
| WO | 9925417 A1 | 5/1999 |
| WO | 9944666 A2 | 9/1999 |
| WO | 0197743 A2 | 12/2001 |
| WO | 2004049970 A2 | 6/2004 |
| WO | 2006014631 A1 | 2/2006 |
| WO | 2006135853 A2 | 12/2006 |
| WO | 2007001701 A1 | 1/2007 |
| WO | 2007022592 A1 | 3/2007 |
| WO | 2008013441 A1 | 1/2008 |
| WO | 2010070685 A1 | 6/2010 |
| WO | 2011133736 A2 | 10/2011 |
| WO | 2014/003809 A1 | 1/2014 |
| WO | 2014134215 A1 | 9/2014 |
| WO | 2014152191 A1 | 9/2014 |
| WO | 2015/006828 A1 | 1/2015 |
| WO | 2015035393 A1 | 3/2015 |
| WO | 2015191685 A1 | 12/2015 |
| WO | 2016149653 A2 | 9/2016 |
| WO | WO-2016149653 A2 * | 9/2016 ....... A61B 17/12036 |
| WO | 2017210584 A1 | 12/2017 |
| WO | 2019095049 A1 | 5/2019 |
| WO | 2020033372 A1 | 2/2020 |

OTHER PUBLICATIONS

European Search Report Issued May 31, 2022 in European Application No. 19846055.2.

Int'l Search Report and Written Opinion issued 2019 in Int'l Application PCT/US19/45252.

Holcomb et al., "Causes of death in US Special Operations Forces in the global war on terrorism: 2001-2004," Annals of Surgery, vol. 245, No. 6, pp. 986-991 (2007).

Sohn et al., "Demographics, Treatment, and Early Outcomes in Penetrating Vascular Combat Trauma," Arch Surg, vol. 143, No. 8, pp. 783-787 (2008).

White et al., "The Epidemiology of Vascular Injury in the Wars in Iraq and Afghanistan," Annals of Surgery, vol. 253, No. 6, pp. 1184-1189 (2011).

Fenton et al., "Comparing risks of alternative medical diagnosis using Bayesian arguments," J. Biomed. Inf., vol. 43, pp. 485-495 (2010).

Patel et al., "Bayesian Designs for Device Clinical Trials," MDG Forum, Waltham, MA., Nov. 3, 2010, downloaded from web page: <http://www.cytel.com/pdfs/Patel_Bayes_Devices_Slides_11.18.10.pdf>.

Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.

Sandgren et al., "The Diameter of the Common Femoral Artery in Healthy Human: Influence of Sex, Age, and Body Size," Journal of Vascular Surgery, vol. 29, No. 3, pp. 503-510 (1999).

SAM II et al., "Blunt Traumatic Aortic Transection: Endoluminal Repair with Commercially Available Aortic Cuffs," Journal of Vascular Surgery, vol. 38, No. 5, pp. 1132-1135 (2003).

Stannard et al., "Resuscitative Endovascular Balloon Occlusion of the Aorta (REBOA) as an Adjunct for Hemorrhagic Shock," J. Trauma, vol. 71, pp. 1869-1872 (2011).

Ledgerwood et al., "The Role of Thoracic Aortic Occlusion for Massive Hemoperitoneum," J Trauma, vol. 16, No. 8, pp. 610-615 (1976).

Langewouters et al., "The static elastic properties of 45 human thoracic and 20 abdominal aortas in vitra and the parameters of a new model," Journal of Biometrics, vol. 17, No. 6, pp. 425-435 (1984).

(56) References Cited

OTHER PUBLICATIONS

Hughes, "Use of an Intra-Aortic Balloon Catheter Tamponade for Controlling Intra-Abdominal Hemorrhage in Man," Surgery, vol. 36, pp. 65-68 (1954).
Chen et al., "The Renal Length Nomogram: A Multivariable Approach," The Journal of Urology, vol. 168, pp. 2149-2152 (Nov. 2002).
Office Action issued Dec. 14, 2023 in EP Application No. 19846055.2.
Extended Search Report issued May 10, 2023 in European Application No. 22743436.2.
Office Action issued Jun. 20, 2023 in U.S. Appl. No. 17/563,669.
Examination Report issued Mar. 28, 2024 in CA Application No. 3107489.

* cited by examiner

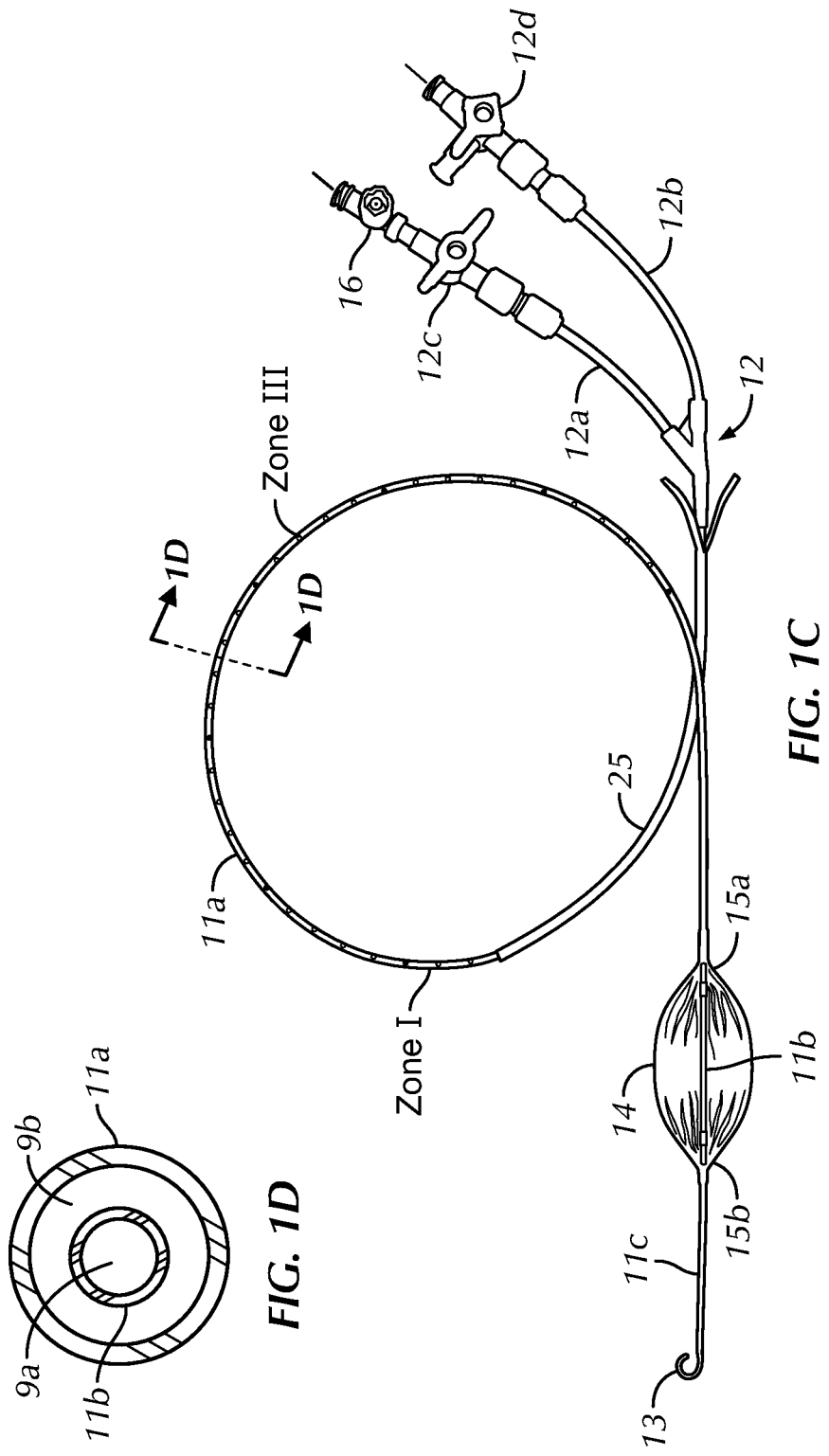

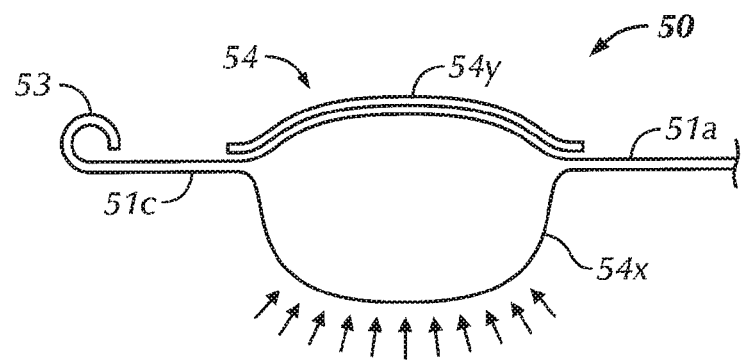
FIG. 13
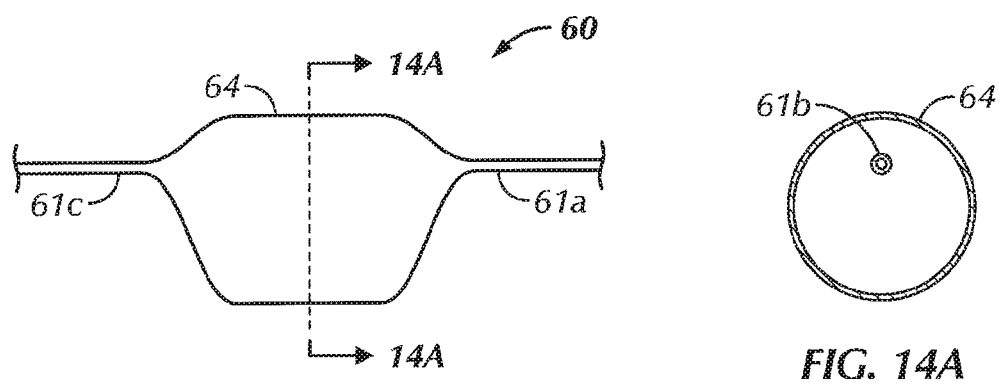
FIG. 14
FIG. 14A
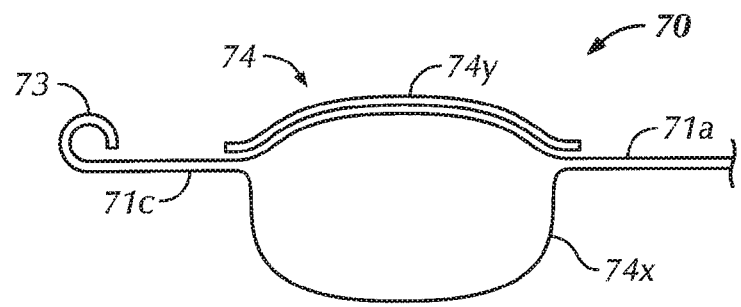
FIG. 15

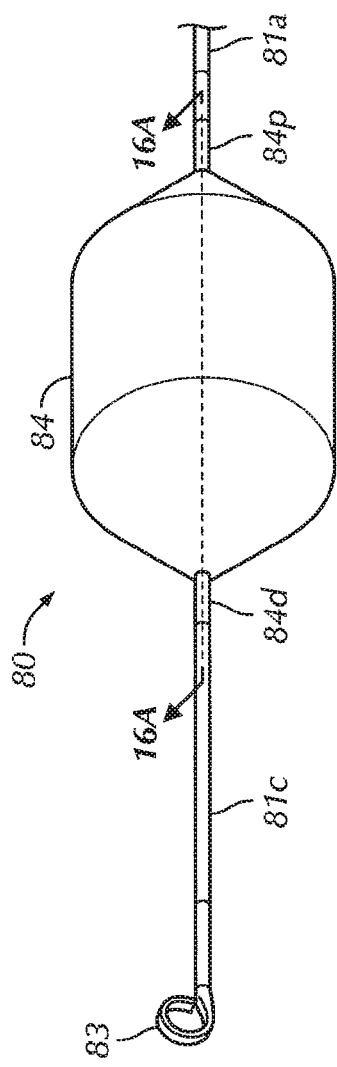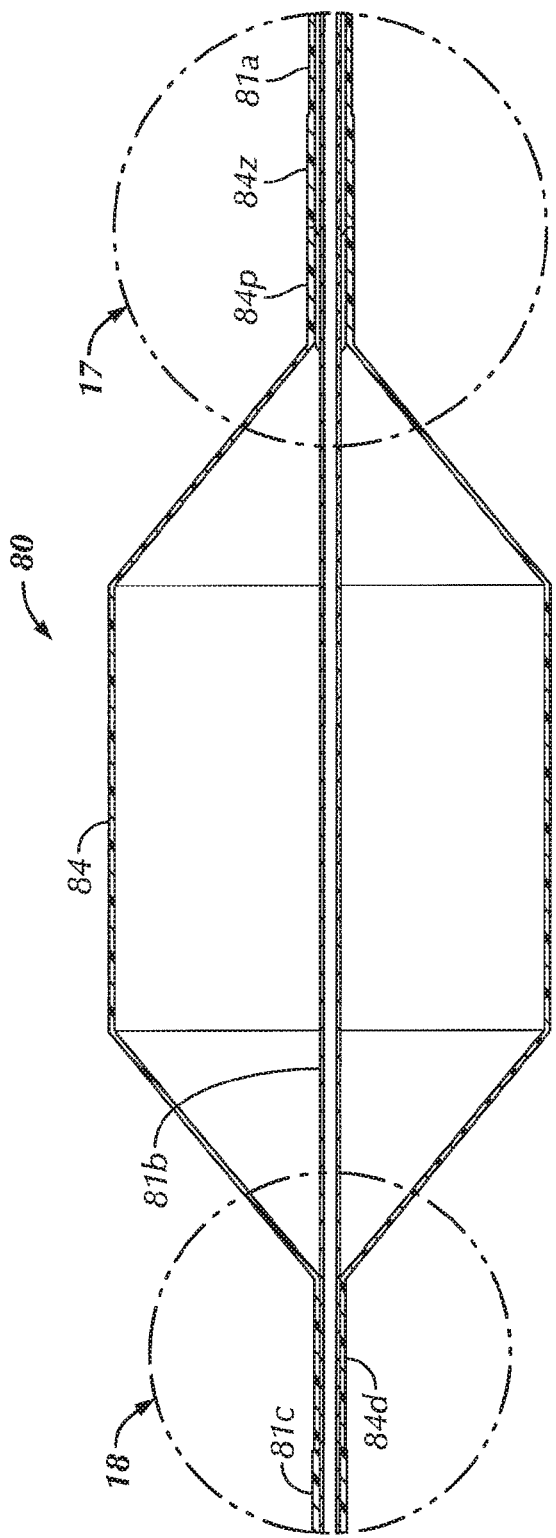

OCCLUSION CATHETER SYSTEM FOR FULL OR PARTIAL OCCLUSION

CROSS-REFERENCE TO RELATED APPLICATIONS

This application is a Section 371 of International Application No. PCT/US2019/045252, filed Aug. 6, 2019, which was published in the English language on Feb. 13, 2020 as International Publication No. WO 2020/033372 A1, which claims priority to U.S. Provisional Application No. 62/714,863, filed on Aug. 6, 2018. The entire contents of these applications are incorporated by reference herein in their entireties.

BACKGROUND OF THE INVENTION

The present invention pertains generally to vascular occlusion catheters and methods of vascular pre-conditioning while controlling occlusion and perfusion during an occlusion procedure. Pre-conditioning is employed to mitigate ischemia before, during and/or after a vascular occlusion procedure, as well as used to reduce or ameliorate the onset of hypertension during or reduce or ameliorate the onset of hypotension after a vascular occlusion procedure. Vascular occlusions may be indicated in either the venous system and/or the arterial system. Endoarterial occlusion is a procedure in which a blood vessel is at least partially occluded in order to restrict blood flow upstream or downstream of the occlusion site for purposes of a vascular procedure or repair. It is known that transient hypertension is a risk factor in arterial occlusion, particularly aortic occlusion. Transient hypertension occurs when the blood pressure upstream of the occlusion site rises to a potentially unsafe level during the time duration of the occlusion. Upon completion of a procedure requiring arterial occlusion, particularly aortic occlusion, care must be taken during the process of reestablishing blood flow to reduce or ameliorate the onset of hypotension. Thus, arterial occlusion carries with it two twin risks, hypertension during the occlusion and hypotension as the occlusion is withdrawn and blood flow restored that must be managed. Partial occlusion of the aorta is also preferred to mitigate the risk of ischemia below the site of the occlusion to limit or eliminate lack of blood flow to organs and tissue below the occlusion location.

In addition to hypotension and hypertension, techniques allowing partial flow of blood and related fluids past the occlusion member may be desirable to provide at least partial blood flow to portions of the patient's body downstream of the occlusion member. At least partial perfusion past the occlusion member can provide the benefits of focusing or directing a majority of blood flow to the brain, heart and lungs or other upstream portions of the patient, but also potentially increasing the amount of time the occlusion member can be implanted in the patient, by providing at least partial blood flow to the patient's organs downstream of the occlusion member, such as to the patient's liver, digestive tract, kidneys and legs.

Referring to FIG. 1PA, partial perfusion may be accomplished by reducing the size of an occlusion member or occlusion balloon 1 that is attached to a catheter 2. The occlusion balloon 1 may, for example, be partially deflated to allow blood to flow between outer surfaces 1a of the occlusion balloon 1 and inner surfaces 3a of a vessel 3 within which the occlusion balloon 1 is positioned. This, for example, deflation of the occlusion balloon 1 may cause the occlusion balloon 1 to lose contact with the inner surface 3a of the vessel 3, thereby causing movement of the occlusion balloon 1 and partial vibration between the vessel 3 and the occlusion balloon 1 that is undesirable. Such loss of contact with the inner surfaces 3a of the vessel 3 by the occlusion balloon 1 is represented in FIG. 1PA, by a cylindrical channel 4 defined between the outer surface 1a of the occlusion balloon 1 and the inner surfaces 3a of the vessel 3. Loss of contact with the inner surface 3a of the vessel 3 by the occlusion balloon 1 may also result in the occlusion balloon 1 and attached catheter 2 being urged downstream in the vessel 3, thereby moving the occlusion balloon 1 out of its preferred placement. It would be desirable to design, develop and implement an occlusion balloon catheter that maintains contact with the vessel 3 during partial perfusion to reduce or eliminate such vibrations and movement of the occlusion member during partial perfusion.

Temporary aortic occlusion as an operative method to increase proximal or central perfusion to the heart and brain or other major organs in the setting of shock due to major trauma is generally known. Despite potential advantages over thoracotomy with aortic clamping, resuscitative endovascular balloon occlusion of the aorta ("REBOA") for trauma has not been widely adopted.

Many attempts have been made at developing technologies to control non-compressible abdominal hemorrhage. For example, non-occlusive, abdominal tamponade procedures have been developed to address the problem of non-compressible hemorrhage, such as introducing an expandable, biocompatible foam into the abdominal cavity to apply pressure to the abdominal organs and vasculature. Pharmacological efforts have also been developed to address the problem of non-compressible hemorrhage. Conventional REBOA procedures are typically performed in an operating room and with the aid of fluoroscopy or other imaging.

Devices that automate inflation and deflation of a balloon are generally known. Intra-aortic balloon counterpulsation catheters for blood pressure augmentation coordinated with electrocardiography signals are also known. Over-inflation safety devices are also known, such as a pressure-relief valve coupled to an inflation lumen that opens when pressure within the inflation lumen exceeds a threshold pressure, but relative pressure within the occlusion balloon is necessary to maintain occlusion of the blood vessel.

It would be desirable to design, develop and implement a system that intermittently and automatically releases an occlusion balloon or member by releasing apposition of the occlusion balloon or member against the vascular wall and allowing perfusion past the occlusion balloon or member in response to a physiological parameter, then re-establishing occlusion in response to potential changes in the physiological parameter, either during a vascular repair procedure to control hypertension or post-repair procedure to control hypotension. It would also be desirable to design, develop and implement a system that allows perfusion past the occlusion balloon or member while maintaining engagement between the occlusion balloon or member and the walls of the vasculature, preferably an artery and more preferably the aorta, to prevent vibration, movement, sliding or shifting of the occlusion balloon or member as blood flows past the occlusion balloon. In addition, it is desirable to design, develop and implement an occlusion balloon that permits relatively fine control of a pressure ratio between proximal and distal sides of the occlusion balloon and, therefore, relatively fine control of blood flow across the occlusion balloon through the vessel. The preferred embodiments of the present invention address certain of these limitations of the prior art occlusion systems.

In addition, it is desirable to design, develop and implement an occlusion balloon that permits relatively fine control of a pressure ratio between proximal and distal sides of the occlusion balloon and, therefore, relatively fine control of blood flow across the occlusion balloon through the vessel. Existing occlusion balloons are difficult to modulate pressure drop across the balloon and modulation can result in movement of the balloon under blood pressure in the balloon. A relatively small change in balloon volume or internal pressure often results in drastic changes in blood pressure between proximal and distal sides of the occlusion balloon, resulting in full occlusion or a relatively high rate of volumetric blood flow across the balloon. It is desirable to design, develop and deploy an occlusion system that is less sensitive to slight pressure changes in the occlusion balloon and provides a more gradual change in blood flow past the occlusion balloon. It is also desired to create catheters with occlusion members that perform both partial and full occlusion. This would allow more gradual transitions between full and no occlusion and also provide surgeons more time to prevent fatal loss of blood in patients. The preferred present invention addresses these shortcomings of prior art occlusion balloons.

A majority of catheters with balloons attached thereto or integrated therewith are bonded together using a lap or overlap weld, wherein the material of the balloon overlaps an end or portion of the catheter. The overlapped portions are then welded or otherwise bonded together to secure the balloon to the catheter. This lap weld causes the profile of the catheter to be greatest at the lap weld because of the overlap of material in this area of the catheter system. Any increase in the size or diameter of the catheter shaft results in an increase in size or counterpart dimension of an introducer sheath through which the catheter is introduced into the patient's body. Alternatively, the catheter shaft may be necked or have a reduced diameter portion at its end where the overlap weld is located in attempts to maintain the overall diameter of the catheter system at the lap weld. This necking of the catheter shaft, however, reduces the flow of inflation medium into and out of the balloon through a reduced diameter internal catheter shaft lumen at the necking area, which is undesirable. In addition, the thickness of the catheter shaft and balloon material may only be reduced to dimensions that allow the catheter and balloon to support the pressures expected within the catheter and the balloon, so that reducing the thickness of the catheter or balloon material is limited by these structural performance parameters. It would be desirable to design, construct and implement a balloon catheter system that minimizes the thickness of the catheter shaft in the weld or connection area with the balloon, while maintaining the size of the internal lumen that extends through this area of the catheter.

BRIEF SUMMARY OF THE INVENTION

Non-compliant or semi-compliant balloons may have certain advantages in REBOA procedures, such as ease of use, because the non-compliant or semi-compliant nature of the balloon causes the internal balloon pressure to increase dramatically once slack in the folds of the non-compliant or semi-compliant balloon is overcome during inflation. Compliant balloons may also be preferred for use in certain REBOA procedures, such as partial occlusion of a vessel where an oversized balloon is inserted into the vessel.

The preferred catheter systems described herein perform partial and full occlusion of a patient's vessel, preferably a large vessel such as various locations in the patient's aorta, including the descending thoracic aorta and the abdominal aorta. A variety of compliant, semi-compliant and non-compliant balloons may be utilized with the preferred occlusion catheter systems to occlude or partially occlude relatively large vessels in the patient's circulatory system. The preferred compliant, semi-compliant and non-compliant balloons preferably perform well during smooth control tests, preferably exhibiting the ability to gradually transition pressure in the vessel between full and no occlusion, such that transition between full and partial occlusion of the vessel is readily controllable to avoid quick or immediate transitions between full occlusion and virtually no occlusion in the vessel.

Certain non-compliant or semi-compliant balloons were relatively easy to use because of the non-compliant or semi-compliant nature of the balloon, which caused the internal balloon pressure to increase dramatically once the "slack" was taken out of the balloon during inflation. While the non-compliant or semi-compliant balloons were effective for performing full occlusion in the tubes or virtual vessels up to, but not exceeding, their blown diameter, these non-compliant balloons generally cannot occlude tubes larger than their blown diameter or at least somewhat larger than their blown diameter, because the non-compliant balloons do not stretch significantly in the radial direction to come into facing engagement with a full diametric slice or portion of the internal walls of the vessel.

As a preferred example of testing a non-compliant or semi-compliant balloon with the preferred occlusion catheter systems, a non-compliant or semi-compliant balloon with a blown diameter of twenty millimeters (20 mm) and a blown length of twenty millimeters (20 mm) was able to partially occlude a simulated vessel comprised of a tube having a fifteen and one-half millimeter (15.5 mm) inner diameter. In contrast, the same twenty millimeter (20 mm) non-compliant or semi-compliant balloon had a limited ability to gradually transition between partial and full occlusion in a simulated vessel comprised of a tube having a nineteen millimeter (19 mm) inner diameter. As the non-compliant or semi-compliant balloon is inflated, the folds of the twenty millimeter (20 mm) balloon in in the fifteen and one-half millimeter (15.5 mm) tube or simulated vessel defines flow channels with the inner surfaces of the tube or vessel that permit some flow to go past the balloon, even when the outer surface of the balloon is touching the wall of the tube or simulated vessel. In contrast, in the nineteen millimeter (19 mm) tube or simulated vessel, there are very few flow channels created by the folds in the balloon because nearly all of the folds are expanded at this greater diameter, so partial occlusion of the tube or simulated vessel is limited. The twenty millimeter (20 mm) diameter non-compliant or semi-compliant balloon also does not substantially occlude a tube or simulated vessel larger than approximately twenty millimeters (20 mm). The twenty millimeter (20 mm) non-compliant or semi-compliant balloon, accordingly, is not preferred for REBOA procedures when the patient's vessel has an inner diameter in the range of twenty to thirty or more millimeters (20-30+ mm).

In the above-described preferred catheter system example, the occlusion balloon is constructed of a low-compliance, semi-compliant or non-compliant polyethylene terephthalate ("PET") balloon, but is not so limited. The occlusion balloon may also be constructed of a nylon, urethane, polyether block amide ("PEBA") or PEBAX material or other similar materials. When the example catheter system is used in vessels or sample vessels smaller in diameter than the blown diameter, the blood vessel or sample vessel is the only material pushing back radially when the balloon inflates. The blood vessel can tolerate some stretching but too much can rupture or cause a dissection. The user preferably stops inflating before this pressure gets too high or a safety feature is incorporated into the catheter system to prevent over-inflation of the occlusion balloon, such as a pop-off or pressure release valve.

In a preferred embodiment, a relatively large diameter, such as a blown diameter of approximately twenty-five to thirty-five millimeters (~25-35 mm), non-compliant or semi-compliant balloon is mounted near the distal end of the catheter system. A pressure-relief or pop-off valve is mounted at the catheter hub in line or in fluid communication with the balloon inflation lumen at a location of the catheter shaft, hub, extension line, stopcock or proximal to the stopcock of the catheter system to prevent the balloon from overinflating.

The relatively large diameter, non-compliant or semi-compliant balloon, such as, but not limited to, having a blown diameter of approximately twenty-five to thirty-five millimeters (~25-35 mm), would have folds in almost all aortas. Greater than ninety-five percent of normal aortas have a diameter of twenty-five millimeters (25 mm) or smaller, so the relatively large diameter balloon would have folds when encountering the inner walls of the aorta during inflation or before full inflation. Accordingly, the relatively large non-compliant or semi-compliant balloon incorporated into the system or a non-compliant or semi-compliant balloon that is configured to have a blown diameter of approximately ten to sixty percent (10-60%) greater than an inner diameter of the associated vessel is functional for partially occluding the vessels, particularly for partial occlusion utilizing folds in the partially inflated balloon to create flow channels with the inner surface of the vessel. The non-compliant or semi-compliant, twenty-five to thirty-five millimeter (~25-35 mm) occlusion balloon, specifically is generally effective for a majority of aortas. The pressure relief valve preferably prevents the user from overinflating the balloon, which could cause aortic rupture/dissection or balloon rupture, but still allow all aortas, generally regardless of size, to be occluded. The preferred catheter system also include a P-tip, hypotube/wire positioned centrally within the catheter system, marks on the outer shaft for placement of the occlusion balloon in a preferred zone of the aorta, no guidewires, and maker bands for visualization of the placement of the balloon.

In a preferred embodiment, the occlusion catheter system is configured for full or partial occlusion of a vessel having a vessel diameter. The occlusion catheter system includes a proximal catheter shaft having a proximal lumen and a hypotube positioned partially within the proximal lumen and spaced from the proximal catheter shaft. The hypotube may also be described as a central shaft. The central shaft may have an internal lumen or may be substantially solid between its proximal and distal ends with both configurations of the central shaft providing strength and stiffness to the preferred catheter for insertion into the patient's vessel. The catheter system also includes a distal catheter shaft attached to a distal end of the hypotube and an occlusion balloon connected at a proximal end to the proximal catheter shaft and at a distal end to the distal catheter shaft. The occlusion balloon has a blown diameter greater than the vessel diameter. The occlusion balloon is configured to define flow channels with inner surfaces of the vessel at folds in the occlusion balloon when the occlusion balloon is partially inflated and in engagement with the inner surfaces.

BRIEF DESCRIPTION OF THE SEVERAL VIEWS OF THE DRAWINGS

The foregoing summary, as well as the following detailed description of preferred embodiments of the instrument, system and method of the present application, will be better understood when read in conjunction with the appended drawings. For the purposes of illustrating the preferred occlusion catheter system, there are shown in the drawings preferred embodiments. It should be understood, however, that the application is not limited to the precise arrangements and instrumentalities shown. In the drawings:

FIG. 1C is a top plan view of a first preferred occlusion catheter system including the first preferred occlusion balloon of FIG. 1;

FIG. 1D is a cross-sectional view of a proximal catheter shaft of the occlusion catheter system, taken along line 1D-1D of FIG. 1C;

FIG. 13 is a side elevational view of a distal portion of a catheter system in accordance with a fifth preferred embodiment of the present invention;

FIG. 14 is a side elevational view of an occlusion balloon of a catheter system in accordance with a sixth preferred embodiment of the present invention;

FIG. 14A is a cross-sectional view of the occlusion balloon of FIG. 14, taken along line A-A of FIG. 14;

FIG. 15 is a side elevational view of a distal portion of a catheter system in accordance with a seventh preferred embodiment of the present invention;

FIG. 16 is a side perspective view of an occlusion catheter system in accordance with an eighth preferred embodiment of the present invention;

FIG. 16A is a cross-sectional view of the occlusion catheter system of FIG. 16, taken along line 16A-16A of FIG. 16;

DETAILED DESCRIPTION OF THE INVENTION

Figure 1P:
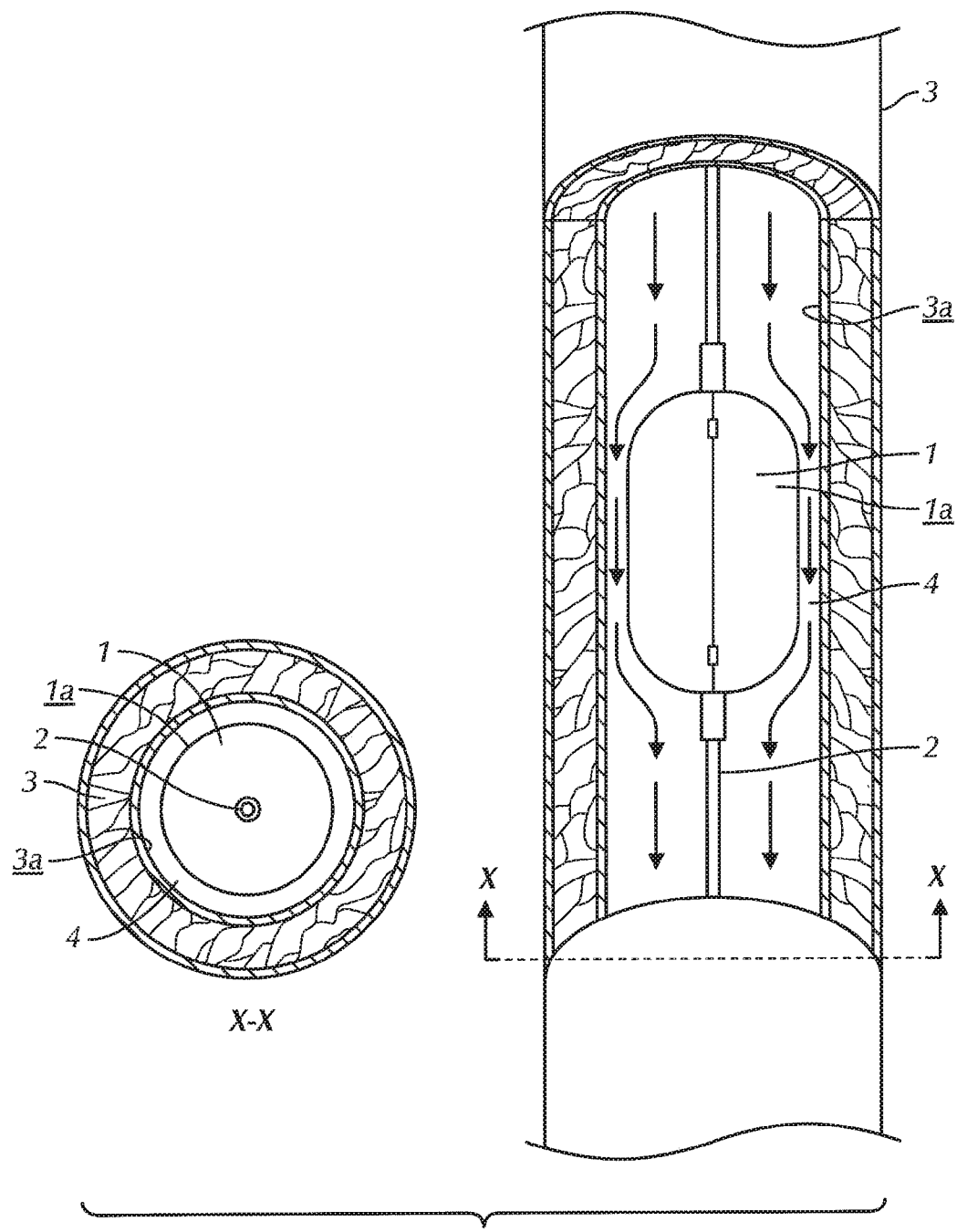
FIG. 1PA is a side perspective, partially cut-away view of a prior art occlusion balloon catheter implanted in a vessel with partial inflation allowing flow around an entire periphery of the occlusion balloon and a cross-sectional view taken along line X-X of the vessel and catheter.
Figure 1:
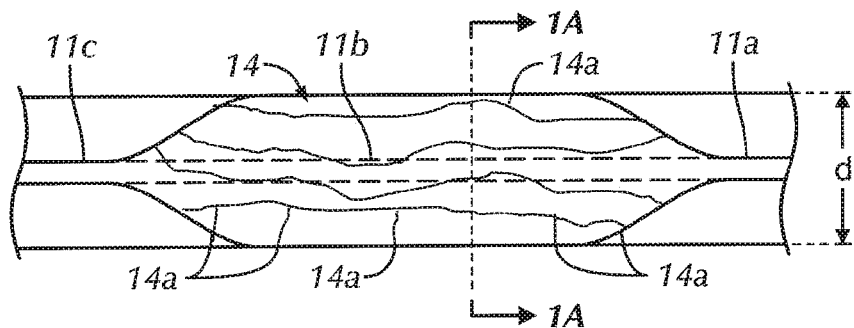
FIG. 1 is a magnified, side elevational view of a non-compliant or semi-compliant occlusion balloon in a simulated vessel in accordance with a first preferred catheter system of the present invention, wherein the occlusion balloon is inflated to come into contact with the simulated vessel, with folds formed in the balloon, thereby creating flow channels.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred occlusion catheter systems and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-4, a first preferred embodiment of an occlusion catheter system, generally designated 10, includes a proximal catheter shaft 11a, a strong and stiff central shaft or hypotube 11b and a distal catheter shaft 11c. The proximal catheter shaft 11a has a central lumen that surrounds a proximal end of the central shaft 11b and is attached to an inflation hub 12 at its proximal end. In the first preferred embodiment, the central shaft 11b is a hypotube 11b with an internal lumen, typically for collecting pressure data via pressure head, delivering medications or instruments to the distal end of the occlusion catheter system 10 or otherwise providing a lumen to the distal end of the system 10. The central shaft 11b may be solid or have the central lumen of the hypotube 11b and preferably provides strength and stiffness to the system 10 in both configurations.

Marker bands 11m are preferably attached to the hypotube 11b proximate proximal and distal ends of the occlusion balloon 14 for location and identification of the position of the occlusion balloon 14 using fluoroscopy or other visualization techniques or systems. The proximal catheter shaft 11a also preferably includes depth markings 33 on its external surface that assists the user in properly placing the catheter system 10 during use by indicating the depth of insertion, as indicated by the depth markings 33. The distal catheter shaft 11c includes an atraumatic tip or a P-tip 13 that unfolds to a generally straight insertion configuration when the catheter is inserted into a vessel 3 and a biased or relaxed configuration when positioned within the patient's vessel 3. An occlusion balloon 14 is connected at a proximal end to an open distal end of the proximal catheter shaft 11a and at a distal end to the distal catheter shaft 11c. A proximal sensor 15a is positioned adjacent the proximal end of the balloon 14 and a distal sensor 15b is positioned adjacent the distal end of the balloon 14. The proximal and distal sensors 15a, 15b are preferably comprised of pressure sensors and may be electronic pressure sensors positioned directly on the catheter shaft, a port for a fluid lumen for measuring pressure based on pressure head, a separate pressure sensor positioned adjacent the catheter shaft or other pressure sensing mechanisms or methods that facilitate pressure or other measurement at the desired locations. The balloon 14 is preferably comprised of a large diameter, semi-compliant or non-compliant balloon 14. A pressure-relief or pop-off valve 16 is preferably connected to a catheter hub 16 at the proximal end of the proximal catheter shaft 11a. The pressure-relief or pop-off valve 16 may be positioned in close relation to the or on the inflation hub 12, such as proximal to the balloon valve or stopcock 12c in a molded pressure relief fitting. The pressure-relief or pop-off valve 16 can be used to prevent the balloon 14 from overinflating.

In the first preferred embodiment of the occlusion catheter system 10, the occlusion balloon 14 is comprised of a semi-compliant or substantially non-compliant balloon mounted to the proximal and distal catheter shafts 11a, 11c.

Figure 1A:
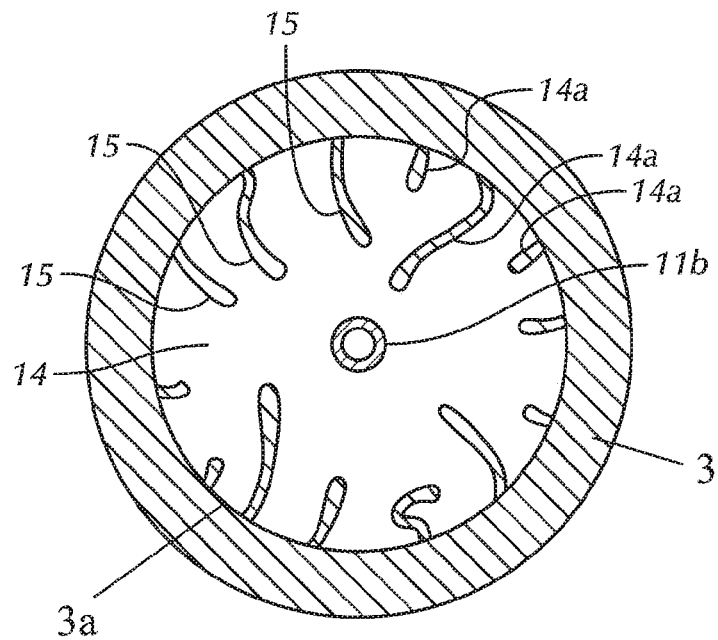
FIG. 1A is a cross-sectional view of the balloon of FIG. 1 inflated to a partially occluded configuration, taken along line X-X of FIG. 1.
Figure 1B:
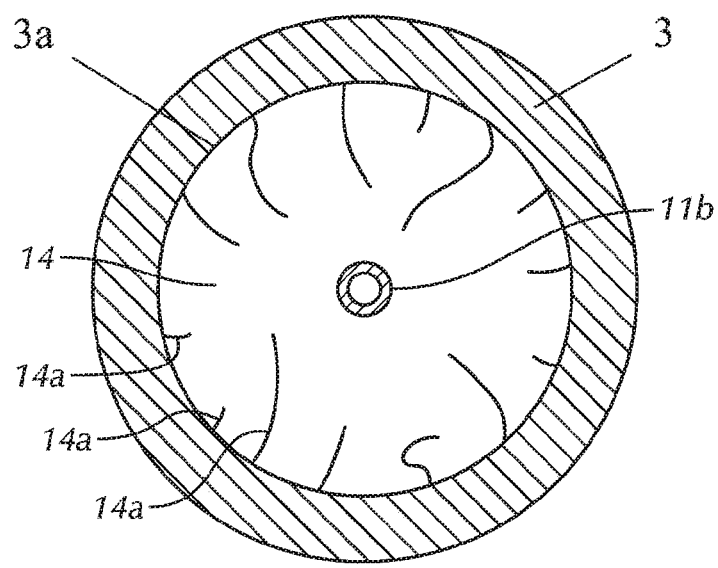
FIG. 1B is a cross-sectional view of the balloon of FIG. 1 inflated to a full occlusion configuration, taken along line X-X of FIG. 1.

Although not so limited, a non-compliant or semi-compliant balloon 14 generally has growth of approximately two to seven percent (2-7%) within the working range (balloon pressure) when inflated, a semi-compliant balloon has growth of approximately seven to twenty percent (7-20%) within the working range (balloon pressure) when inflated and a compliant balloon has growth of approximately greater than twenty percent (20%+) within the working range (balloon pressure) when inflated. Compliant balloons 14 may have growth of approximately one to three hundred percent (100-300%) within the working range (balloon pressure) when inflated. The occlusion balloon 14 has a relatively large blown diameter D, preferably approximately twenty-five to thirty-five millimeters (~25-35 mm), that is configured to be approximately ten to sixty percent (10-60%) larger than the vessel 3 into which the balloon 14 is inserted and inflated for occlusion. The semi-compliant balloon 14 is, therefore, only partially inflated when its outer surface comes into full diametric contact with the inside of the target vessel 3 and folds 14a remain at the outer surface of the balloon 14. In this partially inflated configuration, the semi-compliant balloon 14 has a partially inflated diameter d, wherein the folds 14a are formed. These folds 14a create channels 15 with the inner surfaces of the vessel 3 or with portions of the outer surface of the balloon 14 that allow partial perfusion or blood flow past the balloon 14 under the blood pressure within the vessel 3. The cross-hatching within the folds 14a of FIG. 1A represent blood or fluid flowing through the folds 14a, although the folds 14a would otherwise be open in this partially inflated configuration.

The preferred pressure-relief valve 16 mounted to the catheter hub 12 is configured to prevent the balloon 14 from overinflating so that the balloon 14 does not burst and the vessel 3 is not damaged during the procedure. In the first preferred embodiment, the pressure-relief valve 16 is mounted in the fluid flow path further from the occlusion balloon 14 than the stopcock or balloon valve 12c. If the pressure relief valve 16 is mounted closer to the occlusion balloon 14 in the fluid flow path for inflation of the occlusion balloon 14, the pressure relief valve 16 remains active or able to relieve pressure during the occlusion period. Momentary pressure increases in the vessel 3 during the occlusion period may result in release of pressure by the pressure-relief valve 16. The system 10, however, is not significantly impacted by positioning the pressure-relief valve 16 closer to the occlusion balloon 14 in the fluid flow than the stopcock or balloon valve 12c and is not limited to being positioned either further way from or closer to the occlusion balloon 14 in the fluid flow than the stopcock or balloon valve 12c.

In the partially inflated configuration when the outer surface of the balloon 14 initially engages the inner surfaces 3a of the vessel 3 (FIG. 1A), the large diameter, semi-compliant balloon 14 has the folds 14a in almost all aortas, approximately greater than ninety-five percent (95%) of the patient population of aortas, which allows for partial occlusion utilizing the oversized, semi-compliant balloon 14 in nearly all patient aortas. The folds 14a and the inner walls of the vessel 3 define channels 15 that facilitates blood flow past the occlusion balloon 14. The pressure relief valve 16 preferably prevents the user from overinflating the balloon 14, thereby preventing aortic rupture/dissection or rupture of the balloon 14, but still allowing nearly all patient population aortas, to be occluded.

The preferred catheter system 10 may include the proximal and/or distal pressure sensors 15a, 15b, flow sensors, temperature sensors and other sensors that collect data related to the procedure above and/or below the balloon 14. The system 10 may also include a display on the inflation hub 12 or otherwise positioned for review by the user that is in wired or wireless contact with the pressure sensors 15a, 15b and other sensors so that the user is able to monitor the procedure and characteristics of the patient during the procedure. The use of the pressure sensors 15a, 15b and the related sensors with a controller or control hub 200 may also facilitate closed loop control of the catheter system 10 during use to modulate balloon volume to achieve a desired set point (i.e. proximal/distal blood pressure, temperature, flow, etc.). The pressure sensors 15a, 15b may be comprised of pressure sensors that measure pressure by fluid pressure head, electronic pressure sensors or other sensors that are able to measure pressure of fluid in the patient's vessel 13, within the occlusion balloon 14 or otherwise within the system 10.

Figure 2:
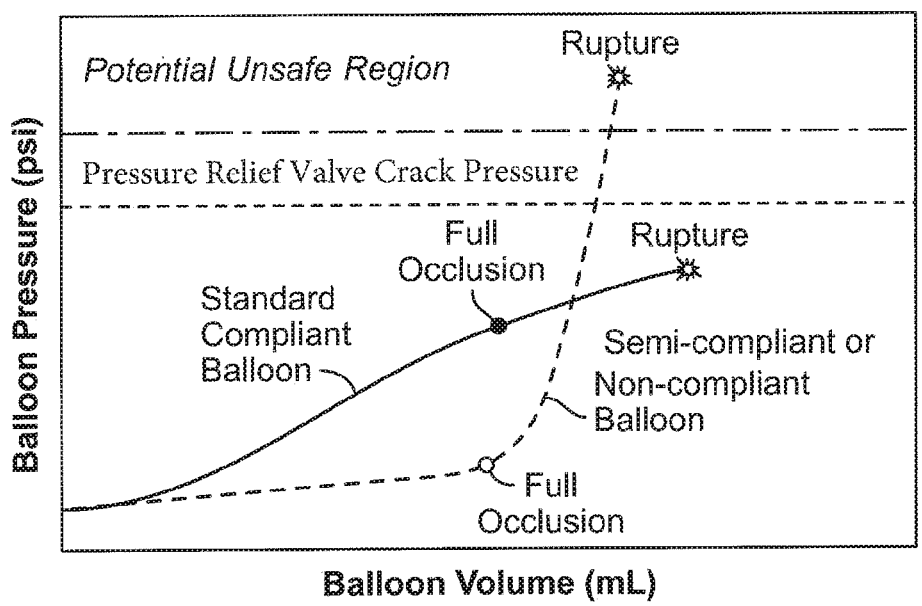
FIG. 2 is a line chart comparing balloon volume vs. balloon pressure for compliant, semi-compliant and non-compliant occlusion balloons mounted on the first preferred catheter system.
Figure 2A:
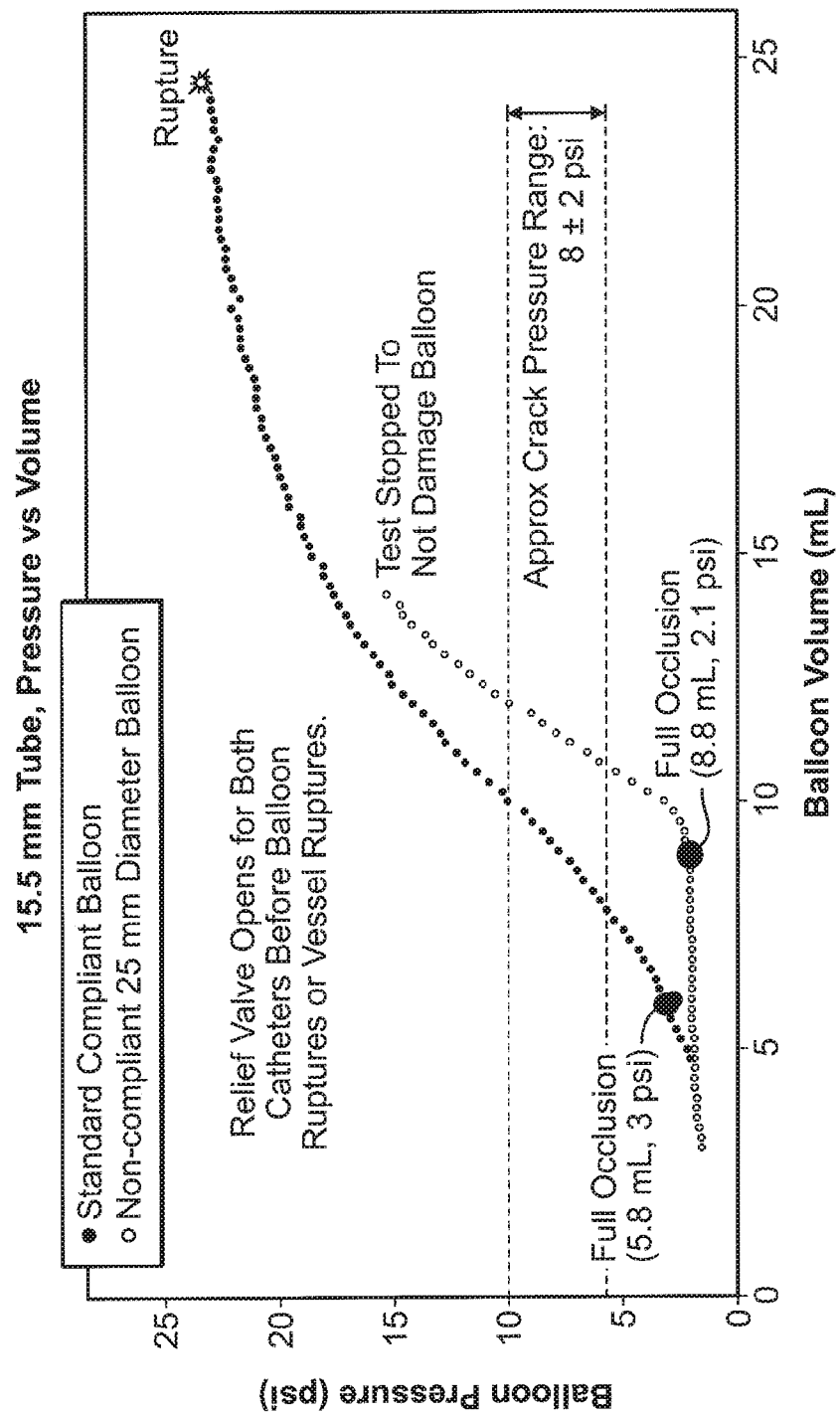
FIG. 2A is a line chart comparing balloon volume vs. balloon pressure for a standard compliant and twenty-five millimeter (25 mm) non-compliant or semi-compliant occlusion balloons mounted in a fifteen and one-half millimeter (15.5 mm) simulated vessel.
Figure 2B:
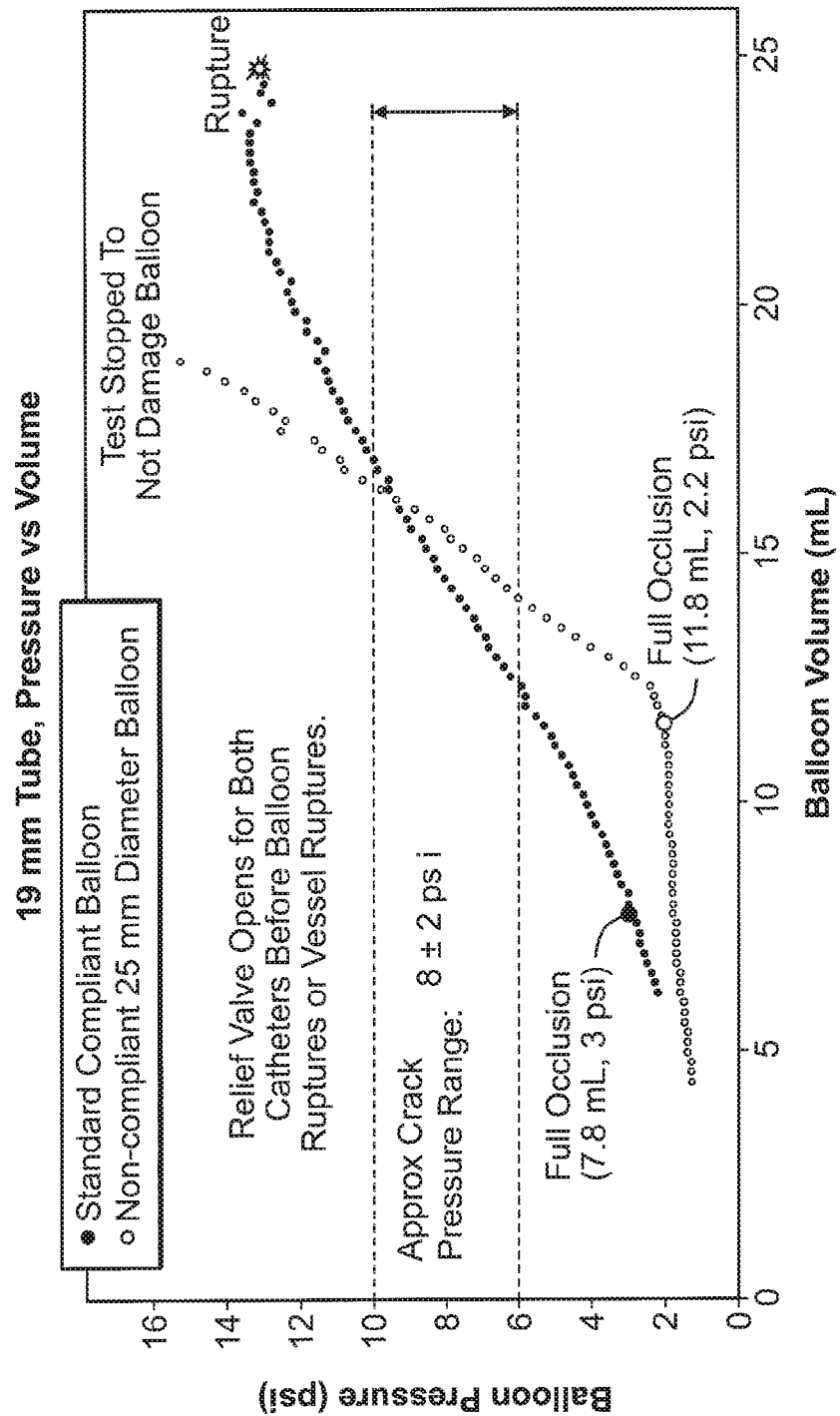
FIG. 2B is a line chart comparing balloon volume vs. balloon pressure for a standard compliant and twenty-five millimeter (25 mm) non-compliant or semi-compliant occlusion balloons mounted in a nineteen millimeter (19 mm) simulated vessel.

The combination of the pop-off or pressure-relief valve 16 and the non-compliant, semi-compliant or compliant balloon 14, which is properly sized for the vessel 3, allow the user to inflate the balloon 14 safely until the pop-off or pressure-relief valve 16 releases liquid or other inflation medium, as shown in FIG. 2-2B. The preferred occlusion catheter system 10 is configured for all reasonable vessel 3 sizes or diameters of the aorta, generally up to approximately twenty-eight and six tenths millimeters (~28.6 mm). Then when deflating from full occlusion and approaching full occlusion, the folds 14a in the balloon 14 open enough to allow some blood flow in the channels 15 defined by the folds 14a and/or the inner surfaces 3a of the vessel 3, thereby providing the user with a good degree of partial occlusion to limit shock to the patient's system of a quick change in pressure above and below the balloon 14. Specifically, as is shown in FIGS. 2-2B, the non-compliant or semi-compliant balloon 14 exhibits a slow and gradual increase in internal balloon pressure during an initial balloon volume increase and then a sharp increase in pressure with limited increase in balloon volume or inflation fluid introduction after full occlusion. The range of inflation fluid introduction and removal near full occlusion is, therefore, relatively forgiving for the non-compliant or semi-compliant balloon 14 just below full occlusion pressures and volumes, when oversized for the associated vessel 3, allowing the user to readily control partial occlusion below the full occlusion range. The compliant balloon 14 has a more consistent balloon pressure vs. balloon volume slope below and above full occlusion when oversized for the associated vessel 3. When properly sized and configured, the compliant, semi-compliant and non-compliant balloons 14 of the preferred occlusion catheter system 10 provide partial and full occlusion and are prevented from rupture of the balloon 14 and rupture of the vessel 3 by pressure release from the pop-off or pressure-relief valve 16. The semi-compliant or non-compliant balloon 14 also provides a clear tactile indication to the user that the balloon 14 has come into direct facing engagement with the inside surfaces of the vessel 3 that provides an opposite reaction force to the expanding occlusion balloon 14 or has reached its full blown diameter D based on the steep pressure increase with relatively little inflation medium introduction into the balloon 14, as shown in FIG. 2. This facilitates the pressure-relief valve 16 releasing pressure well below an unsafe region of inflation where vessel 3 rupture or balloon rupture could potentially occur.

Figure 2C:
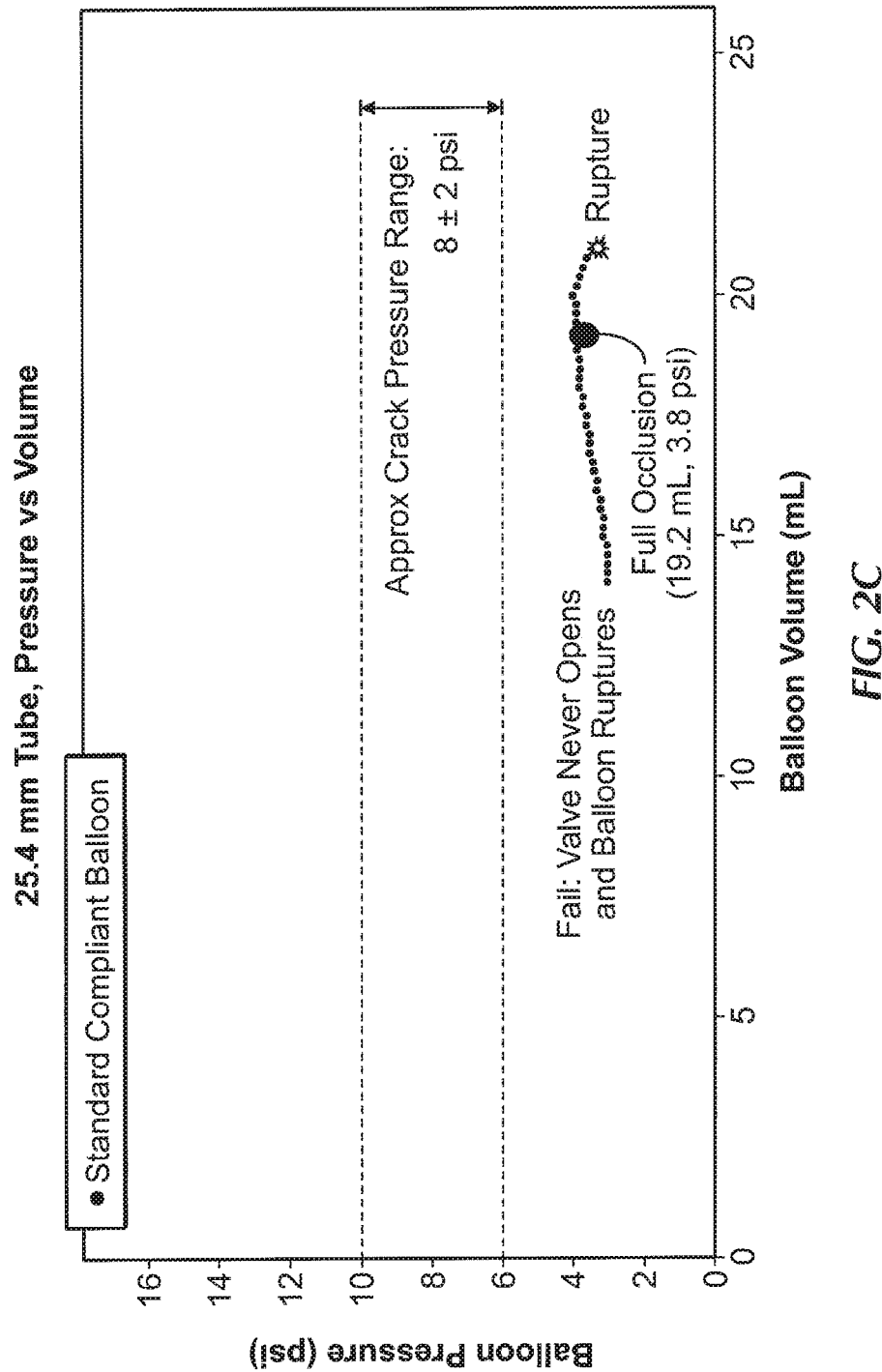
FIG. 2C is a line chart comparing balloon volume vs. balloon pressure for a standard compliant occlusion balloon mounted in a twenty-five and four tenths millimeter (25.4 mm) simulated vessel.

Referring to FIGS. 2-2C, balloon volume in milliliters (mL) vs. balloon pressure in pounds per square inch (psi) are shown for various occlusion balloon and vessel 3 configurations and scenarios. FIG. 2 shows generic compliant and semi-compliant or non-compliant balloon pressure vs. balloon volume curves wherein the compliant balloon 14 stretches enough to soften at the point when the vessel 3 is occluded and, thus, may rupture before the crack pressure of the pop-off or pressure-relief valve 16 is reached (FIG. 2C), while the non-compliant or semi-compliant balloon 14 actuates the pressure-relief or pop-off valve 16 before either the balloon 14 or vessel 3 rupture. FIG. 2A, shows a non-compliant or semi-compliant twenty-five millimeter (25 mm) balloon 14 and a prior art compliant balloon 14 that both actuate the pressure-relief or pop-off valve 16 before either balloon or vessel 3 rupture. The balloons 14 of FIG. 2A are inserted and actuated in a fifteen and one-half millimeter (15.5 mm) tube or simulated vessel 3 and the pressure-relief or pop-off valve 16 has an actuation range of eight pounds per square inch with a tolerance of two pounds per square inch (8 psi±2 psi). The compliant balloon 14 reaches full occlusion of the vessel 3 at approximately five and eight tenths milliliters (5.8 mL) and three pounds per square inch (3 psi), while the non-compliant or semi-compliant balloon 14 reached full occlusion of the vessel 3 at approximately eight and eight tenths milliliters (8.8 mL) and two and one tenth pounds per square inch (2.1 psi).

FIG. 2B, shows the same non-compliant or semi-compliant and compliant balloons 14 inflated in a nineteen millimeter tube or simulated vessel 3 with the same the pressure-relief or pop-off valve 16 having the same actuation range of eight pounds per square inch with a tolerance of two pounds per square inch (8 psi±2 psi). The compliant balloon 14 reaches full occlusion of the vessel 3 at approximately seven and eight tenths milliliters (7.8 mL) and three pounds per square inch (3 psi), while the non-compliant or semi-compliant balloon 14 reached full occlusion of the vessel 3 at approximately eleven and eight tenths milliliters (11.8 mL) and two and two tenths pounds per square inch (2.2 psi). Both the compliant and non-compliant or semi-compliant balloons 14 enter the pop-off range prior to rupture, thereby actuating the pop-off or pressure-relief valve 16 before the balloon ruptures.

FIG. 2C, shows the same compliant balloon 14 inflated in a twenty-five and four tenths millimeter (25.4 mm) tube or simulated vessel 3 with the same pressure-relief or pop-off valve 16 having the same actuation range of eight pounds per square inch with a tolerance of two pounds per square inch (8 psi±2 psi). In the scenario and configuration of FIG. 2C, the pressure in the compliant balloon 14 never exceeded the crack pressure of the pop-off or pressure relief valve 16, so the valve 16 does not open and the balloon 14 ruptures. For smaller vessels 3, for example, approximately twenty millimeters (20 mm) or smaller, the compliant and non-compliant or semi-compliant balloons 14 function similarly (i.e. pressure in the balloons 14 stays low through full occlusion, then starts to increase quickly after full occlusion has been reached). When vessels 3 are larger than about twenty millimeters (20 mm), the compliant balloons 14 no longer have this rapid increase in balloon pressure after full occlusion. The reason is the balloon 14 has stretched enough at that point that the balloon 14 is becoming less stiff as additional volume is added. This results in the balloon pressure staying relatively low, all the way to rupture. This configuration and scenario doesn't allow the pop-off valve 16 to open before balloon 14 ruptures, because the pressure is too low to actuate the pop-off valve 16. This effect is highly depending on the blown diameter D of the balloon 14 in comparison to the size. If, as a non-limiting example, a compliant balloon was blown to thirty millimeters (30 mm) and placed in a relatively small vessel 3, such as a fifteen millimeter (15 mm) vessel 3, it is possible that the balloon wouldn't have stretched much by the time it reaches full occlusion and the pressure would rise significantly like a non-compliant or semi-compliant balloon. Both a compliant and non-compliant or semi-compliant balloons could work for this application if it was blown significantly large.

For relatively small vessels 3, such as the fifteen and one-half and nineteen millimeter (15 mm and 19 mm) tubes or simulated vessels 3, shown in FIGS. 2A and 2B, the compliant and non-compliant or semi-compliant balloons 14 have relatively similarly shaped pressure vs. volume curves. In these simulations, the compliant balloon 14 hasn't significantly stretched when the compliant balloon 14 reaches full occlusion, such that the wall of the compliant balloon 14 is still relatively thick and the pressure in the balloon 14 rises relatively quickly, similar to the non-compliant or semi-compliant balloon 14, although the slope of pressure increase of the non-compliant or semi-compliant balloon 14 is steeper starting at a greater inflation fluid volume. Conversely, for large diameter vessels 3 where the compliant balloon 14 is not oversized for the vessel 3, the compliant balloons 14 can have a shallow slope and the pressure doesn't increase significantly after occlusion, thereby potentially leading to rupture at a relatively low pressure (FIG. 2). This configuration could lead to the compliant balloon 14 rupturing before the pop-off valve 16 is actuated. For the pop-off valve 16 to function successfully, meaning the valve 16 always opens before balloon 14 or vessel 3 rupture, the valve 16 remains closed or unactuated during inflation of the balloons 14 to full occlusion and the valve 16 opens or is actuated before either: (1) the balloon 14 ruptures or the blood vessel 3 ruptures.

Figure 4:
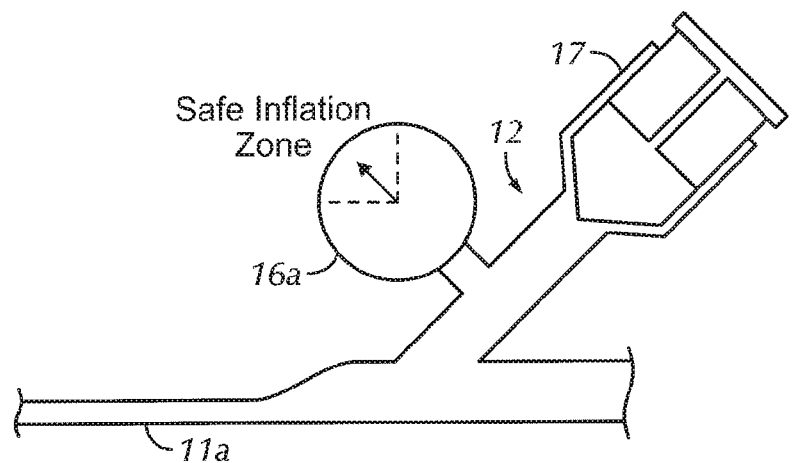
FIG. 4 is a magnified, cross-sectional view of a pressure gauge mounted to the catheter system of FIG. 3.
Figure 5:
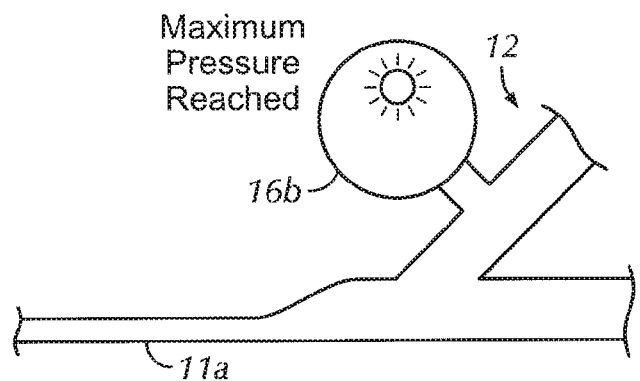
FIG. 5 is a magnified, cross-sectional view of a threshold pressure sensor mounted to the catheter system of FIG. 3.

Referring to FIGS. 4 and 5, the preferred occlusion catheter system 10 may alternatively include a pressure gauge 16*a* (FIG. 4) or a threshold pressure sensor 16*b* (FIG. 5) mounted to the hub 12 for monitoring the pressure within the balloon 14. The pressure gauge 16*a* may include markings or indications related to a safe inflation zone or range for the associated balloon 14 and the threshold pressure sensor 16*b* may include a visual indication to notify the user that a maximum pressure has been reached within the balloon 14. The threshold pressure sensor 16*b* may also indicate to the user that the threshold pressure has been reached by a light, a buzzer, vibration emission or another related indication to the user that the threshold pressure is reached.

Figure 3:
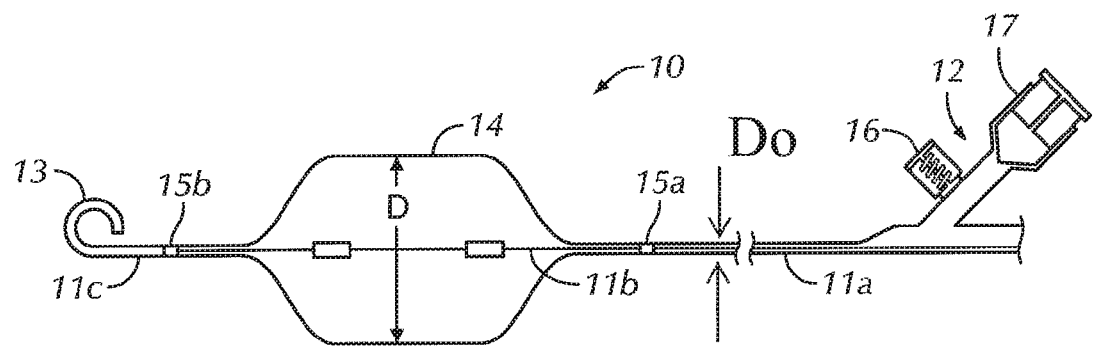
FIG. 3 is a side, cross-sectional view of the catheter system in accordance with the first preferred embodiment of the present invention.
Figure 6:
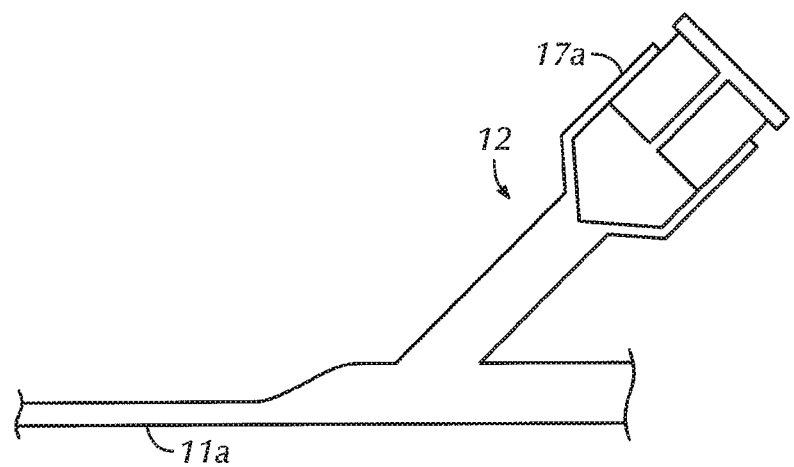
FIG. 6 is an alternative pressure source that may be utilized with the catheter system of FIG. 3.

Referring to FIGS. 3, 4 and 6, the first preferred occlusion catheter system 10 includes an inflation pressure source 17 that is preferably comprised of a syringe that may be manually operated by the user. The system 10 is not limited to including the inflation pressure source 17 comprised of the syringe and may include a compressor or other pressure introducing mechanism that is able to provide a pressurized inflation medium into the occlusion balloon 14 through the proximal catheter shaft 11*a*, which may be controlled by the user manually or via a controller. The system 10 may, alternatively, include a comparatively large syringe 17*a* with a large bore to limit the amount of pressure that can be inserted into the balloon 14 by a users hand.

Figure 7:
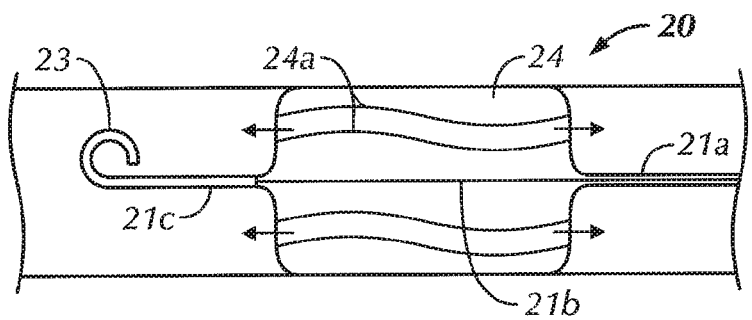
FIG. 7 is a side, cross-sectional view of a distal portion of a catheter system in accordance with a second preferred embodiment of the present invention.

Referring to FIG. 7, a second preferred occlusion catheter system 20 has a similar construction to the first preferred occlusion catheter system 10 and like reference numbers are utilized to identify like features of the second preferred occlusion catheter system 20 with a number "2" prefix replacing the "1" prefix to distinguish the features of the occlusion catheter system 10 of the first preferred embodiment from the occlusion catheter system 20 of the second preferred embodiment.

In the second preferred occlusion catheter system 20, a complaint, large-diameter balloon 24 is mounted to the proximal and distal catheter shafts 21a, 21c in place of the non-compliant or semi-compliant balloon 14 of the first preferred embodiment. When the compliant balloon 24 is inflated in a vessel 3 smaller than the blown diameter D, the folds 24a in the balloon 24 create flow channels for good partial occlusion. When full occlusion has been reached, the balloon 24 stretches axially to facilitate additional inflation medium volume in the balloon 24 without causing the blood vessel 3 to stretch further, as shown in FIG. 7. In addition, the greater length in the contact between the outer surfaces of the balloon 24 and the inner surfaces 3a of the vessel 3 facilitate full occlusion of the vessel 3 as the folds 24a are released or removed as the balloon 24 stretches.

Figure 8:
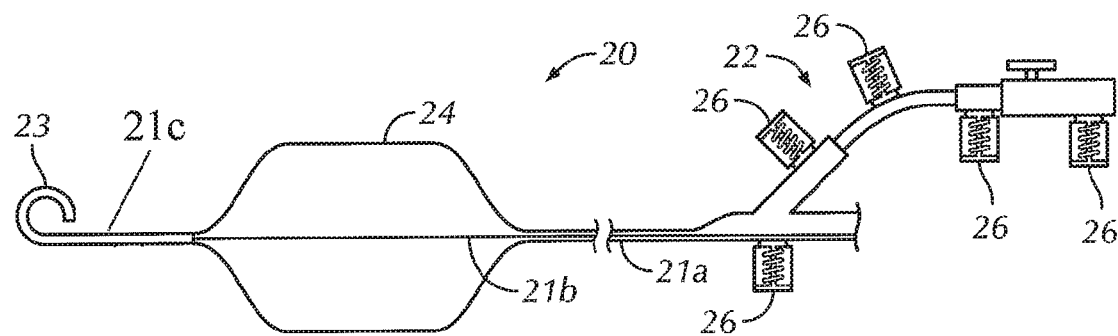
FIG. 8 is a side elevational view of the catheter system of FIG. 7.

Referring to FIG. 8, the second preferred catheter system 20, as well as the first preferred catheter system 10, may mount the pop-off or pressure-relief valve (not shown) at various locations on the proximal or distal catheter shafts 21a, 21c or on the hub 22. The pop-off or pressure-relief valve may be mounted nearly anywhere on the catheter system 20 that permits communication between the valve and the inflation medium that inflates the balloon 24. For example, the pop-off or pressure-relief valve, as well as the pressure gauge or sensor 16a and the threshold pressure sensor 16b, may be located at the catheter hub 22, in-line with the balloon extension line, at the balloon pressure relief fitting, proximal to the stopcock, on the catheter shaft or near the balloon.

Figure 9:
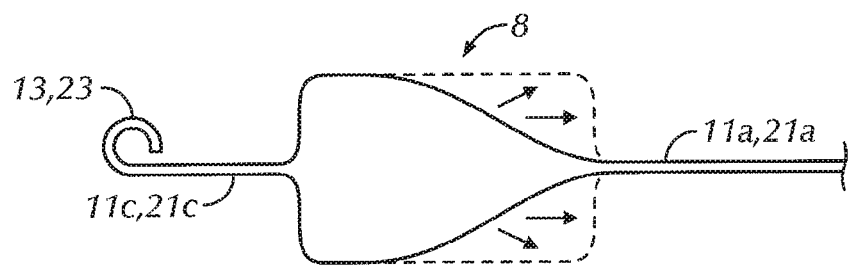
FIG. 9 is a side elevational view of a first alternative preferred occlusion balloon that may be utilized with any of the preferred catheter systems described herein.
Figure 10:
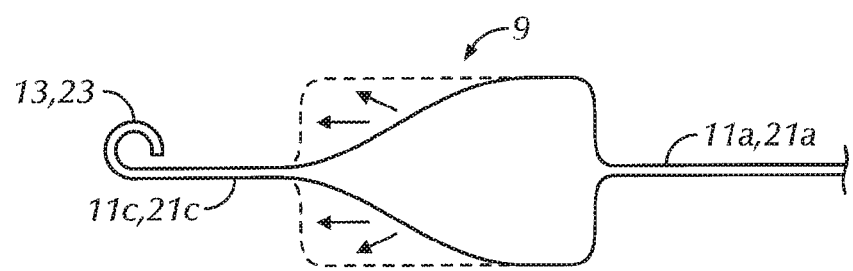
FIG. 10 is a side elevational view of a second alternative preferred occlusion balloon that may be utilized with any of the preferred catheter systems described herein.

Referring to FIGS. 9 and 10, first and second alternative occlusion balloons 8, 9 may be mounted to any of the preferred occlusion catheter systems, including the first and second preferred occlusion catheter systems 10, 20, described herein. The first and second alternative occlusion balloon 8, 9 are tapered to create an extended range of partial occlusion by allowing the balloon 8, 9 to grow axially. The first and second preferred tapered balloons 8, 9 reduce the likelihood of the balloons 8, 9 "windsocking" or pushing the balloon fluid or inflation medium to the proximal or downstream side of the balloons 8, 9 near the proximal catheter shaft 11a, 21a when the balloons 8, 9 are in the vessel 3 and subjected to blood pressure within the vessel 3.

Figure 11:
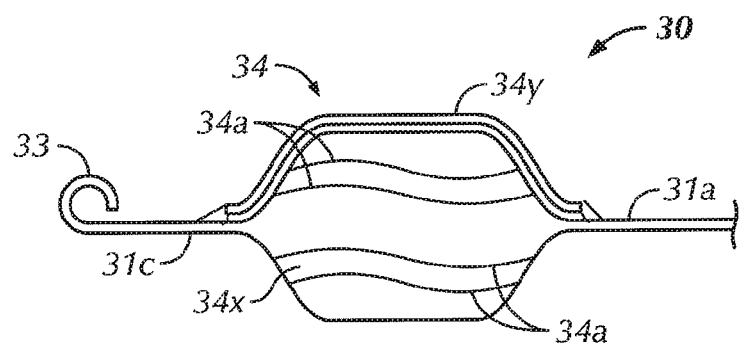
FIG. 11 is a side elevational view of a distal portion of a catheter system in accordance with a third preferred embodiment of the present invention.

Referring to FIG. 11, a third preferred occlusion catheter system 30 has a similar construction to the first and second preferred occlusion catheter systems 10, 20 and like reference numbers are utilized to identify like features of the third preferred occlusion catheter system 30 with a number "3" prefix replacing the "1" and "2" prefixes to distinguish the features of the occlusion catheter systems 10, 20 of the first and second preferred embodiments from the occlusion catheter system 30 of the third preferred embodiment. The third preferred occlusion catheter system 30 includes an occlusion balloon 34 comprised of an oversized, non-compliant or semi-compliant balloon 34x paired with a non-compliant or semi-compliant, smaller diameter spine balloon 34y. In a partially inflated configuration, balloon folds 34a are formed at the outer surface of the oversized, non-compliant or semi-compliant balloon 34x that form flow channels with the inner surfaces 3a of the vessel 3 for partial occlusion capability in small vessels 3. In addition, the spine balloon 34y, the inner surfaces 3a of the vessel 3 and the surfaces of the oversized balloon 34x define flow channels for partial blood flow, particularly when the occlusion balloon 34 is positioned within a large vessel 3.

Figure 12:
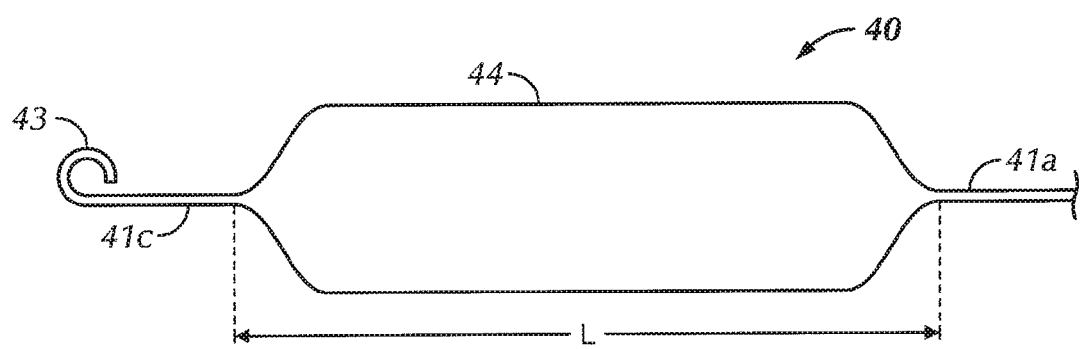
FIG. 12 is a side elevational view of a distal portion of a catheter system in accordance with a fourth preferred embodiment of the present invention.

Referring to FIG. 12, a fourth preferred occlusion catheter system 40 has a similar construction to the first, second and third preferred occlusion catheter systems 10, 20, 30 and like reference numbers are utilized to identify like features of the fourth preferred occlusion catheter system 40 with a number "4" prefix replacing the "1," "2" and "3" prefixes to distinguish the features of the occlusion catheter systems 10, 20, 30 of the first, second and third preferred embodiments from the occlusion catheter system 40 of the fourth preferred embodiment. In the fourth preferred embodiment, a comparatively longer occlusion balloon 44 is mounted to the proximal and distal catheter shafts 41a, 41c. The comparatively longer occlusion balloon 44 is configured to extend the range of partial occlusion because comparatively greater length L makes partial occlusion more gradual. In the fourth preferred embodiment, the occlusion balloon 44 has a length L of approximately thirty to one hundred millimeters (30-100 mm) for occlusion of a typical patient's aorta.

Referring to FIGS. 13-15, fifth, sixth and seventh preferred occlusion catheter systems 50, 60, 70 have a similar constructions compared to the first, second, third and fourth preferred occlusion catheter systems 10, 20, 30, 40 and like reference numbers are utilized to identify like features of the fifth, sixth and seventh preferred occlusion catheter systems 50, 60, 70 with the numbers "5," "6," and "7" prefixes replacing the "1," "2," "3" and "4" prefixes, respectively to distinguish the features of the occlusion catheter systems 10, 20, 30, 40 of the first, second, third and fourth preferred embodiments from the occlusion catheter systems 50, 60, 70 of the fifth, sixth and seventh preferred embodiments. In the fifth, sixth and seventh preferred embodiments, the systems 50, 60, 70 include an offset occlusion balloon 54, 64, 74 mounted to the proximal catheter shaft 51a, 61a, 71a and the distal catheter shaft 51c, 61c, 71c. The offset occlusion balloons 54, 64, 74 could be utilized with any of the preferred occlusion catheter systems 10, 20, 30, 40, 50, 60, 70 described herein. The fifth, sixth and seventh preferred occlusion balloons 54, 64, 74 are designed and configured to strengthen the occlusion balloons 54, 64, 74 where they stretch the most. In the fifth preferred embodiment, the spine balloon 54y inhibits expansion of the oversized occlusion balloon 54x such that the lower part of the oversized occlusion balloon 54x stretches the most. This effect is caused by the restraining nature of the non-compliant or semi-compliant spine balloon 54y limits the occlusion balloon 54x from growing in the direction toward the spine balloon 54y. In the sixth preferred embodiment, the occlusion balloon 64 is constructed of a compliant balloon 64, although the balloon 64 may also be non-compliant or semi-compliant, that is designed and configured or blown such that the occlusion balloon 64 is offset relative to the longitudinal axis defined by the proximal and distal catheter shafts 61a, 61c and the hypotube 61b. In the seventh preferred embodiment, the occlusion balloon 74 is constructed of a non-compliant or semi-compliant oversized and offset occlusion balloon 74x and an adjacent spine balloon 74y. The oversized occlusion balloon 74x is designed and configured to be offset from the longitudinal axis defined by the proximal and distal catheter shafts 71a, 71c and the spine balloon 74y is positioned on the limited diameter side of the oversized occlusion balloon 74x.

Figure 17:
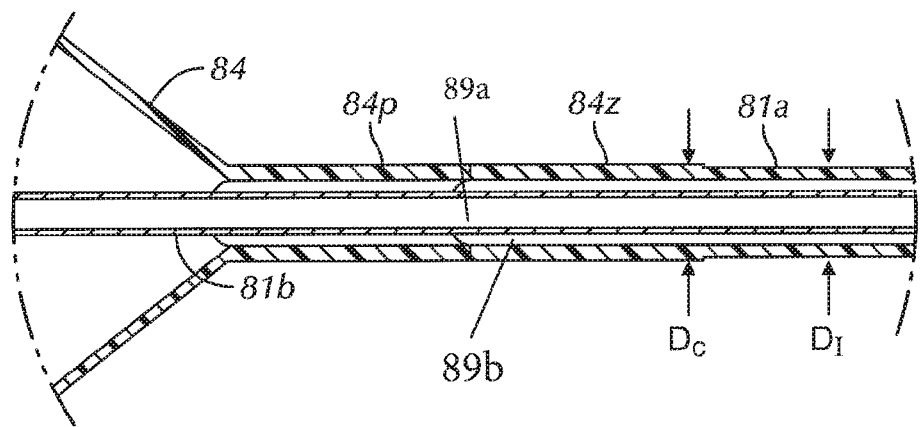
FIG. 17 is a magnified cross-sectional view of a portion of the occlusion catheter system of FIG. 16, taken from within shape 17 of FIG. 16A.
Figure 18:
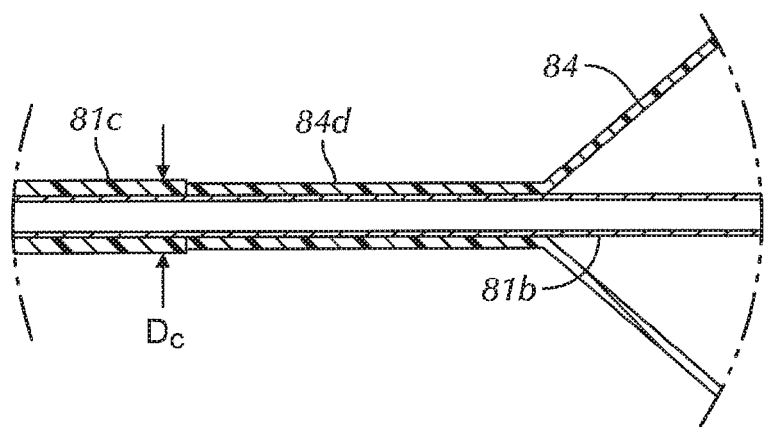
FIG. 18 is a magnified cross-sectional view of a portion of the occlusion catheter system of FIG. 16, taken from within shape 18 of FIG. 16A.

Referring to FIGS. 16-18, an eighth preferred occlusion catheter system 80 has a similar construction to the first, second, third, fourth, fifth, sixth and seventh preferred occlusion catheter systems 10, 20, 30, 40, 50, 60, 70 and like reference numbers are utilized to identify like features of the eighth preferred occlusion catheter system 80 with a number "8" prefix replacing the "1," "2," "3," "4," "5," "6," and "7" prefixes to distinguish the features of the occlusion catheter systems 10, 20, 30, 40, 50, 60, 70 of the first, second, third, fourth, fifth, sixth and seventh preferred embodiments from the occlusion catheter system 80 of the eighth preferred embodiment.

In the eighth preferred embodiment, the occlusion balloon 84 has a proximal end 84p and a distal end 84d. To connect the balloon 84 to the proximal catheter 81a and the distal catheter 84c, the balloon proximal end 84p is butt welded to the proximal catheter 81a (FIG. 17) and the balloon distal end 84d is butt welded to the distal catheter 81c (FIG. 18). Butt welding the balloon proximal and distal ends 84p, 84d to the proximal and distal catheters 81a, 81c maintains an outer diameter Do of the catheter to limit the size of the insertion sheath 18 required for introducing the catheter system 80 into the patient. The outer diameter Do is preferably small enough for insertion into the introducer sheath or insertion catheter 18 having an inner introducer diameter of seven French gauge (7 Fr) or less, such as six French gauge (6 Fr). The seven French (7 Fr) or smaller introducer sheath 18 typically results in the access site through the patient's skin and into the vessel 3 being closed by holding manual pressure for a period of time, such as twenty to thirty minutes (20-30 min). If the introducer sheath 18 has the introducer diameter R greater than seven French (7 Fr), a surgical repair of the access site may be required, thereby further complicating the procedure. In the first preferred embodiment, the outer diameter Do of the proximal catheter shaft 11a and the distal catheter shaft 11c are six French gauge (6 Fr) or less to accommodate sliding through the insertion sheath 18 having the inner diameter of seven French gauge (7 Fr) with the occlusion balloon 14 in the folded configuration and retained by the peel away sheath 25 at a diameter of approximately seven French gauge (7 Fr) or less. The outer diameter Do of six French gauge (6 Fr) or less in combination with the seven French gauge (7 Fr) introducer sheath inner diameter provides an annular space between the proximal catheter shaft 11a and the introducer sheath 18. If the annular gap is flushed and prepared with saline solution, the annular gap facilitates use of fluid column pressure monitoring for measuring blood pressure below the occlusion balloon 14, near the terminus of the introducer sheath 18, if a side arm or port 99 of the introducer sheath 18 is connected to a pressure sensor or monitor 98. The additional pressure monitor (not shown in FIG. 1E) permits the surgeon or medical personnel to measure pressure separate from the pressure sensors 15a, 15b that are on the occlusion catheter system 10. The occlusion catheter system 10 may also include a pressure monitor 98 that is in fluid communication with the hypotube lumen 9a through the arterial line extension line 12b to measure pressure head.

In addition, the butt welding also facilitates maintaining an inner diameter $D_I$ of the proximal catheter 81a such that flow of inflation medium through the space or proximal lumen between the hypotube 81b and the proximal catheter 81a is not limited or constricted at the connection of the balloon proximal end 84p and the proximal catheter shat 81a. At the proximal side of the balloon 84, the balloon proximal end 84p is preferably positioned against the distal end of the proximal catheter 81a and butt welded with the hypotube 81b positioned within a lumen within the proximal catheter 81a and the balloon proximal end 84p that facilitates flow of the inflation medium into and out of the balloon 84. At the distal side of the balloon 84, the balloon distal end 84d is preferably positioned against the proximal end of the distal catheter 81c and butt welded with the balloon distal end 84d. The distal catheter 84c and the distal balloon end 84d are also both preferably in facing engagement with and secured, potentially lap welded, to the hypotube 81b to prevent inflation fluid from escaping the distal end of the balloon 84. Minimizing restriction of the lumen between the lumens within the proximal catheter shaft 81a and the balloon proximal end 84p and the hypotube 81b is preferred to facilitate rapid inflation or filling of the balloon 84 with the inflation medium without causing the pop-off or pressure-relief valve 16 to open prematurely, while also maintaining at low profile of the catheter and facilitating rapid deflation of the balloon 84, if necessary.

The eighth preferred occlusion catheter system 80 may also include a relatively thin reinforcement band 84z that overlaps the butt weld at the connection between the proximal catheter 81a and the balloon proximal end 84p to increase strength and rigidity of the connection without significantly adding to the profile or outer diameter Do of the catheter system 80 at the proximal end of the balloon 84 and of the distal catheter shaft 81c. The reinforcement band 84z may also be utilized at the distal end of the balloon 84 at the butt weld between the distal catheter shaft 81c and the balloon distal end 84d. The outer diameter Do is preferably six French gauge (6 Fr) or less for insertion through the seven French gauge (7 Fr) inner diameter of the introducer sheath 18 to utilize the gap between the outer diameter Do and the inner diameter of the introducer sheath 18 for fluid column pressure monitoring. The diameter at the reinforcement band 84z and the occlusion balloon 14 in the folded configuration is less than seven French gauge (7 Fr) for insertion through the seven French gauge (7 Fr) introducer sheath 18.

Referring to FIGS. 1-6, the occlusion catheter system 10 of the first preferred embodiment is designed to fully or partially occlude the vessel 3 having a vessel diameter $D_V$ accessed with an introducer sheath 18 having an inner introducer diameter $D_R$ of seven French gauge (7 Fr) or less, such as six French gauge (6 Fr). In the first preferred embodiment, the introducer sheath 18 is comprised of a substantially cylindrical sheath that may have a sharpened distal end for insertion through the patient's skin into the vessel 3 and may have a flared or funnel-shaped proximal end for receipt of the straightened P-tip 13, distal catheter shaft 11c, folded occlusion balloon 14, and proximal catheter shaft 11a during the insertion and placement process. The occlusion balloon 14 preferably has a limited thickness to accommodate low-profile the folded configuration for insertion through the seven or six French gauge (7 or 6 Fr) introducer sheath 18 when folded over the central shaft 11b. In the preferred embodiment, the inner introducer diameter $D_R$ of the seven French gauge (7 Fr) introducer sheath 18 is approximately two and thirty-three hundredths millimeters (2.33 mm) and the inner introducer diameter $D_R$ of the six French gauge (6 Fr) introducer sheath 18 is approximately two and zero hundredths millimeters (2.00 mm). The inner introducer diameter $D_R$ is preferred to minimize the puncture in the patient's skin and vessel 3 and to simplify the procedure, as use of introducer sheath's 18 with inner introducer diameters $D_R$ greater than seven French gauge (7 Fr) typically requires additional and specialized medical personnel. The vessel diameter $D_V$ of zones I and III of over ninety-nine percent (99%) of typical patient's is approximately twenty-six millimeters (26 mm) or less such that the balloon blown diameter D of approximately twenty-five to thirty-five millimeters (25-35 mm) and more preferably thirty millimeters (30 mm) will result in full occlusion of the vessel 3 when the semi-compliant occlusion balloon 14 is inflated to the balloon blown diameter D.

The proximal catheter shaft 11a preferably includes a proximal lumen therein formed between inner surfaces of the proximal catheter shaft 11a and outer surfaces of the central shaft 11b. The proximal lumen is preferably in fluid communication with an inflation cavity 14b inside the balloon 14 wherein pressurized fluid is received to blow-up the occlusion balloon 14 during use or to transform the occlusion balloon 14 from the folded configuration, wherein the folded occlusion balloon 14 is folded around the central shaft 11b for insertion through the introducer sheath 18, and the inflated or partially inflated configurations, wherein the occlusion balloon 14 occludes, typically when inflated to the diameter of the blood vessel 3 when the vessel 3 provides an opposition force to further expansion of the occlusion balloon 14, or partially occludes the vessel 13, typically when the folds 14a are retained in the semi-inflated configurations.

The central shaft or hypotube 11b is positioned partially within the proximal lumen of the proximal catheter shaft 11a, thereby defining the proximal lumen for introduction of the inflation fluid and to provide strength and stiffness to the system 10. The central shaft or hypotube 11b may be substantially solid from its proximal to its distal end or may include the hypotube lumen extending therethrough for pressure measurement by pressure head, introduction of medications to the distal end of the system 10 or otherwise for access through the hypotube lumen to the distal end of the system 10 beyond the occlusion balloon 14 during operation when the occlusion balloon 14 is inflated. The central shaft or hypotube 11b extends beyond the distal end of the proximal catheter shaft 11a for connection to the distal catheter shaft 11c and spans through the inflation cavity 14b. The hypotube lumen may also be configured for introduction of a guidewire for placement of the catheter system 10 in the patient's vessel 13.

In the first preferred embodiment, the proximal catheter shaft 11a includes depth markings 33 on an outer surface. The depth markings 33 may be comprised of hashes or line marks at predetermined distances on the length of the proximal catheter shaft 11a, such as markings at every inch or centimeter along the outer surface of the proximal catheter shaft 11a. The depth markings 33 may alternatively be comprised of zone markings, such as zone I and zone III representing locations in the patient's vessel 3, typically the aorta, wherein the occlusion balloon 14 is likely positioned during use. The preferred location of the occlusion balloon 14 in zone I preferably extends from the original of the left subclavian artery to the coeliac artery, zone II preferably extends from the coeliac artery to the most caudal renal artery and zone III preferably extends distally from the most caudal renal artery to the aortic bifurcation.

The inflation hub 12 of the preferred embodiment is connected to a proximal end of the proximal catheter shaft 11a and to a proximal end of the central shaft or the hypotube 11b. The inflation hub 12 includes a balloon extension line 12a and an arterial line extension line 12b that are positioned generally proximally on the catheter. The balloon extension line 12a and the arterial line extension line 12b are preferably comprised of medical tubing with pressure relief fitting and a balloon valve 12c and a monitor valve 12d thereon, respectively. A syringe or other pressurization device may be attached to the pressure relief fitting of the balloon extension line 12a and the arterial line extension line 12b to pressurize the occlusion balloon 14 or connect to the hypotube lumen 9b through the arterial line extension line 12b. The balloon extension line 12a is in fluid communication with the proximal lumen 9a between the inner surfaces of the proximal catheter shaft and the central shaft 11b and the inflation cavity 14b. The balloon extension line 12a also includes the pressure relief valve 16 thereon that is positioned proximally relative to the balloon valve 12c, such that the inflation or balloon valve 12c is positioned closer to the occlusion balloon 14 than the pressure relief valve 16. In operation, the pressure relief valve 16 will release inflation fluid pressure only during inflation of the occlusion balloon 14 when the balloon valve 12c is open. The pressure relief valve 16, therefore, does not operate when the balloon valve 12 is closed. The pressure relief valve 16 is preferably comprised of a ball valve that seats on an O-ring and is urged onto the O-ring by a spring for appropriate sealing when the pressure relief valve 16 is not intended to be in the open position.

In the first preferred embodiment, the occlusion balloon 14 has a proximal end 20a and a distal end 20b. The proximal end 20a is connected to proximal catheter shaft 11a and the distal end 20b is connected to the distal catheter shaft 11c. The occlusion balloon 14 preferably has the blown diameter D of approximately twenty-five to thirty-five millimeters (25-35 mm). The occlusion balloon 14 is positioned in a folded configuration wherein the occlusion balloon 14 is folded around the central shaft or hypotube 11b and an inflated configuration wherein the occlusion balloon 14 is expanded to the blown diameter D. The occlusion balloon 14 is in the folded configuration, the distal catheter shaft 11c and the proximal catheter shaft 11a are movable through the introducer sheath 18 for introduction into the vessel 3. The relatively large occlusion balloon 14, preferably between twenty-five to thirty-five millimeters (25-35 mm), in the folded configuration is insertable through the introducer sheath 18 having the inner introducer diameter $D_I$ of seven French gauge (7 Fr) or less. The procedure to occlude the vessel 3 is substantially less invasive and complicated when utilizing the introducer sheath 18 having the inner introducer diameter $D_I$ of seven French gauge (7 Fr) or less.

In the preferred embodiment, a peel-away sheath 25 is pre-positioned over the occlusion balloon 14 in the folded configuration to maintain the folded configuration. The pressure relief valve 16 is preferably primed before use by attaching an inflation syringe to the pressure relief fitting of the balloon extension line 12a, opening the balloon valve 12c and injecting inflation fluid until the pressure relief valve 16 opens or releases pressure. Since the peel-away sheath 25 is covering the occlusion balloon 14, the occlusion balloon 14 preferably does not inflate. Negative pressure on the syringe plunger will then be applied to remove the remaining fluid/air from the balloon lumen.

The pressure relief valve is a safety feature designed to open and vent inflation medium if the balloon is over-inflated. If the balloon is inflated properly (not over-inflated), the pressure relief valve will not need to open. If the valve does open due to over-inflation, it will shut automatically when the balloon lumen has vented sufficient volume.

This design may be used with a guidewire up to thirty-eight thousandths of an inch (0.038") in diameter if desired. It is still designed to be used without a guidewire, but warnings regarding use with a guidewire will be removed.

The proximal and distal sensors 15a, 15b and potentially a pressure sensor within the occlusion balloon 14, preferably transmit signals to a controller or control hub 200 that may be incorporated into the inflation hub 12 and the pressures are preferably displayed as pressure readings on a display screen or display screens mounted to the occlusion catheter system 10, preferably on the control hub 200 or the inflation hub 12. The control hub 200 is preferably mounted on a proximal portion of the inflation hub 12 and includes the integrated LCD screen to display the pressures from the pressure sensors or other sensors 15a, 15b. The display screen of the control hub 200 may display the pulsatile blood pressures 201, 202, 203, 204 above and/or below the occlusion balloon 14, an occlusion percentage 205 in the vessel 13 or other desired pressure, temperature, pH or related patient or system data acquired from the system 10. The control hub 200 may also include a guidewire orifice 206 that accommodated use of a guidewire. The control hub 200 also preferably includes a power button 207 to turn the control hub 200 off and on during use. The balloon extension line 12a also preferably extends from the control hub 200. The control hub 200 may be configured, operate and function similarly to the control hub described in U.S. patent application Ser. No. 15/573,054, published as U.S. Patent Application Publication No. 2019/0076152 and titled, "System and Method for Low Profile Occlusion Balloon Catheter," which is incorporated herein by reference in its entirety, particularly with respect to the control hub.

Monitoring the pressures displayed on the display screen allows the user to observe blood pressure responses to the various inflation configurations of the occlusion balloon 14, in real time and in a convenient location, as the pressurization of the occlusion balloon 14 is modified. The positioning of the control hub 200 on the inflation hub 12 with the display screen thereon is preferred, versus a vital monitor that may or may not be conveniently located relative to the procedure for observation by the technician or physician. The display of the pressures from the pressure sensors or other sensors 15a, 15b on the display screen with a localized signal processor acts as a means for open-loop feedback of the occlusion catheter system 10. The displays may display the pressure inside the occlusion balloon 14 from an internal balloon pressure sensor, the pressure proximally of the occlusion balloon 14 from the proximal pressure sensor 15a and the pressure distally of the occlusion balloon 14 from the distal pressure sensor 15b. The proximal and distal sensors 15a, 15b are not limited to pressure sensors and may be comprised of alternative sensors for acquiring data related to the system 10 or the patient, such as temperature, pH, flow rate and related data. The senor data may also be transmitted to a central processor in a wired or wireless manner for depiction, manipulation and/or processing. For example, the collected data may be wirelessly transmitted to a remote central processor for storage and depiction on a larger display, such as a television screen, tablet, vital sign monitor or related equipment for viewing by a larger audience, manipulation and recording or storage. The displays may also include other collected data or calculated information for the user, such as a pressure ratio between the distal and proximal pressure sensors 15a, 15b, an indication of the degree or percentage of occlusion of the vessel 3 based on an algorithm that uses the proximal and distal pressures 15a, 15b to provide an approximation of the degree of occlusion. The degree of occlusion could be displayed as a percentage, on a scale, such as 1-5, as a dial gauge or in other manners that provide an estimation of the degree of occlusion to the user.

The control hub 200 on the inflation hub 12 preferably includes the controller and a power source. The power source is preferably comprised of a battery or batteries stored in the control hub on the inflation hub 12 to power at least the display screen. The controller may include a circuit board to process signals, make calculations related to the collected data, control the operating components and perform related functions described herein.

In a non-limiting, preferred example, as conditions change within the patient with the occlusion balloon 14 positioned in the vessel 3 and in the partially or fully inflated configurations, the partial and distal sensors 15a, 15b provide passive feedback to the practitioner to indicate the need for changes to the occlusion balloon's 14 volume to manage blood pressure distal and proximal to the occlusion balloon 14. If the occlusion balloon 14 is inflated in a constricted vessel 3, occlusion may be lost as the vessel 3 relaxes and the passive feedback can indicate to the practitioner that additional volume or pressure is required in the occlusion balloon 14 to maintain occlusion or a desired level of partial occlusion.

Figure 1E:
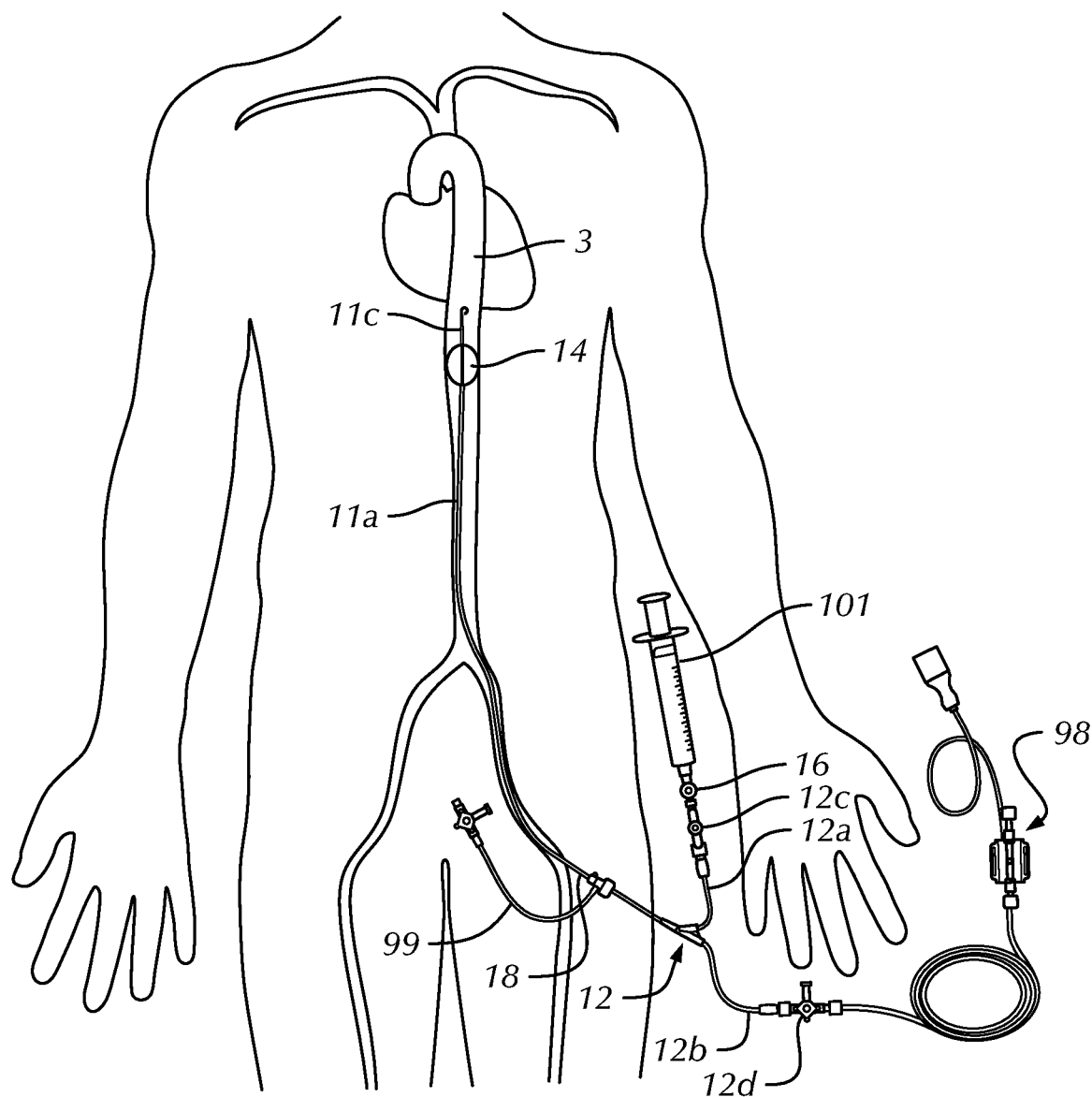
FIG. 1E is a top plan view of the first preferred occlusion catheter system of FIG. 1C implanted in a patient's aorta.
Figure 1F:
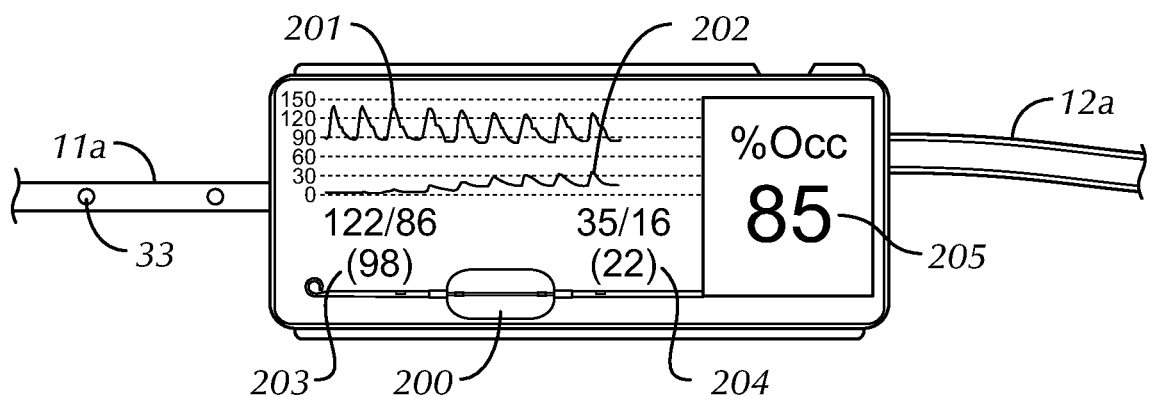
FIG. 1F is a front elevational view of a control hub attached to a proximal catheter shaft of the occlusion catheter system of FIG. 1C.
Figure 1G:
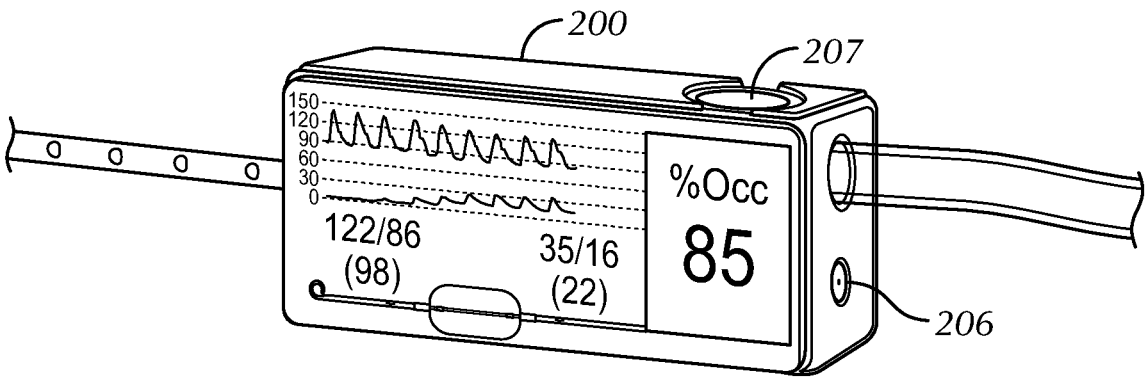
FIG. 1G is a front perspective view of the control hub of FIG. 1F.

In operation in a non-limiting example, the controller 200 is preferably connected to the pressure sensors 15a, 15b and other sensors, as is described herein, for management of the occlusion state of the occlusion balloon 14 in a closed loop configuration (full feedback). The controller 200 is powered on by depressing the power button 207 and can be set to maintain the distal and/or proximal pressures or the pressure ratio between the two by continually adjusting the volume or pressure of the fluid introduced into the occlusion balloon 14 using a preferably small, internal, locally powered pump in the controller 200. The controller 200 may be set to maintain the proximal pressure measured by the proximal pressure sensor 15a at approximately zero when maintaining full occlusion and at a pressure greater than zero when maintaining partial occlusion through creation of the blood flow channels at the folds 14a. For partial occlusion, the controller 200 is preferably set to manage the pressure ratio or a pressure ratio within a range, to maintain a user-specified amount of partial occlusion. The controller 200 may also be configured to permit the user to select a distal pressure setpoint that sets a desired pressure for the distal pressure sensor 15b, which is typically the upstream side of the occlusion balloon 14 when the system 10 is positioned in the artery or vessel 3, such as the aorta (FIG. 1E). The controller 200 preferably adjusts the fluid volume in the occlusion balloon 14 until the setpoint is achieved. The controller 200 may also be based on a proximal side setpoint associated with the proximal pressure sensor 14a or a target degree of occlusion (i.e. a preferred percentage of occlusion or pressure ratio). The balloon valve 12c may be utilized to switch between a manual pressurization of the system 10, wherein pressure is manually introduced into and withdrawn from the occlusion balloon 14 by the user, such as with a syringe 101, and the above-described closed loop feedback configuration, wherein the controller 200 substantially controls the pressure within the occlusion balloon 14.

In the preferred embodiment, the atraumatic tip or p-tip 13 has a generally circular profile and is flexible for positioning in the straightened insertion configuration from the biased circular profile. The atraumatic tip 13 is preferably secured to or co-molded with the distal catheter shaft 11c. The guiding atraumatic tip 13 may be employed with any of the preferred embodiments of the occlusion catheter system 10 described herein. The guiding atraumatic tip 13 is preferably comprised of a polymeric cylindrical or tubular member that has a distal section formed into a generally flattened cylinder having two generally planar opposing surfaces and two generally curved opposing surfaces. The two generally planar opposing surfaces include an inner planar surface and an outer planar surface. The atraumatic tip 13 has a distally extending section that projects distally from the distal catheter shaft 11c and a curved section continuous with the distally extending section that curves away from the central longitudinal axis of the occlusion catheter system 10, then proximally toward the occlusion balloon 14 and subtends a generally circular arc toward the central longitudinal axis of the occlusion catheter system 10. The angle of the curvature may be between about one hundred eighty degrees (180°) and three hundred fifty-five degrees (355°), more preferably between about two hundred seventy degrees (270°) and three hundred fifty degrees (350°) and even more preferably between about three hundred degrees (300°) and three hundred fifty degrees (350°) such that a gap is provided between the terminal end of the generally cylindrical flattened distal section and the more proximal surface of the atraumatic tip 13. The distally extending section and curved section may alternatively be formed as a generally in-plane circular shape or may be formed as an out-of-plane generally helical shape, where a terminal end of the curved section is laterally displaced from the central longitudinal axis of the occlusion catheter system 10. In this manner, the generally flattened distal section is characterized by a generally circular profile It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. An occlusion catheter system for full or partial occlusion of an aorta having an inner diameter, the occlusion catheter system comprising:
    a proximal catheter shaft having a proximal lumen;
    a central shaft positioned partially within the proximal lumen and spaced from the proximal catheter shaft;
    a distal catheter shaft attached to a distal end of the central shaft; and
    an occlusion balloon having a proximal end and a distal end, the occlusion balloon connected at the proximal end to the proximal catheter shaft and at the distal end to the distal catheter shaft, the occlusion balloon being positioned in a folded, uninflated configuration around the central shaft, the proximal catheter shaft, the distal catheter shaft and the occlusion balloon in the folded configuration having an outer diameter less than seven French, and
    the occlusion balloon being constructed of a semi-compliant or non-compliant material and sized to have a blown diameter between approximately ten percent to sixty percent greater than the inner diameter of the aorta, whereby an outer surface of the occlusion balloon comes into diametric contact with an inner surface of the aorta upon partial inflation of the occlusion balloon and folds are formed in the outer surface of the occlusion balloon, the folds defining flow channels with inner surfaces of the aorta or with portions of the outer surface of the occlusion balloon that allow partial blood flow past the occlusion balloon.

2. The occlusion catheter system of claim 1, further comprising:
    an inflation hub connected to a proximal end of the proximal catheter shaft and to a proximal end of the central shaft.

3. The occlusion catheter system of claim 2, further comprising:
    a pressure relief valve attached to the inflation hub, the pressure relief valve in fluid communication with an inflation cavity of the occlusion balloon.

4. The occlusion catheter system of claim 2, wherein the inflation hub includes a balloon extension line and an arterial line extension line, the balloon extension line being in fluid communication with the proximal lumen, and the proximal lumen being in fluid communication with an inflation cavity of the occlusion balloon.

5. The occlusion catheter system of claim 4, wherein the balloon extension line includes an inflation valve and a pressure relief valve, the inflation valve being positioned closer to the occlusion balloon than the pressure relief valve.

6. The occlusion catheter system of claim 4, wherein the central shaft is comprised of a hypotube, the hypotube including a hypotube lumen, the hypotube lumen in fluid communication with the arterial line extension line.

7. The occlusion catheter system of claim 1, wherein the occlusion balloon has a blown diameter of approximately twenty-five to thirty-five millimeters (25-35 mm).

8. The occlusion catheter system of claim 1, wherein the occlusion balloon is configured to fully occlude the aorta in an inflated configuration.

9. The occlusion catheter system of claim 1, wherein the proximal catheter shaft includes depth markings.

10. The occlusion catheter system of claim 9, wherein the depth markings include a zone I range and a zone III range.

11. The occlusion catheter system of claim 1, wherein the blown diameter is approximately thirty millimeters (30 mm).

12. The occlusion catheter system of claim 1, further comprising:
    a pressure sensor attached to the occlusion catheter system.

13. The occlusion catheter system of claim 1, wherein the occlusion balloon has a thickness, the thickness being consistent and limited to accommodate the folded configuration and the folded configuration being low-profile.

14. The occlusion catheter system of claim 1, wherein the occlusion balloon has a length of between approximately thirty millimeters and approximately one hundred millimeters.

15. The occlusion catheter system of claim 1, wherein, further inflation from the partial inflation is configured to press respective fold walls upon one another, to, in turn, collapse the flow channels and prevent blood flow past the occlusion balloon.

* * * * *